US011324747B2

(12) United States Patent
Saiyed et al.

(10) Patent No.: US 11,324,747 B2
(45) Date of Patent: May 10, 2022

(54) METHODS AND COMPOSITIONS FOR MANAGING NEUROINFLAMMATION AND NEURODEGENERATION

(71) Applicant: CENTRE FOR CELLULAR AND MOLECULAR PLATFORMS, Karnataka (IN)

(72) Inventors: Taslimarif Saiyed, Bangalore (IN); Ravi Manjithaya, Bangalore (IN); Murumalla Ravi Kumar, Hyderabad (IN); Suresh Santhi Natesan, Bangalore (IN); Janhavi Pandurangi, Mysore (IN); Aravinda K. Chavalmane, Chickmagalur (IN); Shashank Rai, Mumbai (IN)

(73) Assignee: CENTRE FOR CELLULAR AND MOLECULAR PLATFORMS, Bangalore (IN)

( * ) Notice: Subject to any disclaimer, the term of this patent is extended or adjusted under 35 U.S.C. 154(b) by 0 days.

(21) Appl. No.: 16/308,003

(22) PCT Filed: Jun. 7, 2017

(86) PCT No.: PCT/IB2017/053362
§ 371 (c)(1),
(2) Date: Dec. 7, 2018

(87) PCT Pub. No.: WO2017/212420
PCT Pub. Date: Dec. 14, 2017

(65) Prior Publication Data
US 2019/0255054 A1 Aug. 22, 2019

(30) Foreign Application Priority Data
Jun. 7, 2016 (IN) .............................. 201641019577

(51) Int. Cl.
| | |
|---|---|
| *A61K 31/519* | (2006.01) |
| *A61P 25/28* | (2006.01) |
| *A61P 25/16* | (2006.01) |
| *A61K 9/00* | (2006.01) |
| *A61K 31/167* | (2006.01) |
| *A61K 31/198* | (2006.01) |
| *A61K 31/4439* | (2006.01) |
| *A61K 31/4709* | (2006.01) |
| *A61K 31/506* | (2006.01) |
| *A61K 31/69* | (2006.01) |
| *A61K 38/00* | (2006.01) |
| *A61K 45/06* | (2006.01) |

(52) U.S. Cl.
CPC .......... *A61K 31/519* (2013.01); *A61K 9/0019* (2013.01); *A61K 31/167* (2013.01); *A61K 31/198* (2013.01); *A61K 31/4439* (2013.01); *A61K 31/4709* (2013.01); *A61K 31/506* (2013.01); *A61K 31/69* (2013.01); *A61K 38/005* (2013.01); *A61P 25/16* (2018.01); *A61P 25/28* (2018.01); *A61K 45/06* (2013.01)

(58) Field of Classification Search
CPC ................ A61K 31/167; A61K 31/198; A61K 31/4439; A61K 31/4709; A61K 31/506; A61K 31/519; A61K 38/005; A61K 45/06; A61K 9/0019; A61K 31/69; A61P 25/16; A61P 25/28
See application file for complete search history.

(56) References Cited

U.S. PATENT DOCUMENTS

| | | | |
|---|---|---|---|
| 2012/0172808 A1* | 7/2012 | Soppimath ........... | A61K 9/0019 604/187 |
| 2015/0087653 A1* | 3/2015 | Moussa ................ | A61K 31/506 514/253.06 |

OTHER PUBLICATIONS

Chen X, Wales P, Quinti L, Zuo F, Moniot S, Herisson F, et al. (2015) The Sirtuin-2 Inhibitor AK7 Is Neuroprotective in Models of Parkinson's Disease but Not Amyotrophic Lateral Sclerosis and Cerebral Ischemia. PLoS ONE 10(1): e0116919. doi:10.1371/journal.pone.0116919 (Year: 2015).*
Rosee et al. Cancer Research, vol. 62, pp. 7149-7153. (Year: 2002).*
Outeiro et al. 2007, Science, vol. 317, pp. 516-519. (Year: 2007).*
Oct. 6, 2017 International Search Report issued in International Patent Application No. PCT/IB2017/053362.
Oct. 6, 2017 Written Opinion issued in International Patent Application No. PCT/IB2017/053362.
Andis Klegeris et al. "Non-Steroidal Anti-Inflammatory Drugs (NSAIDS) and Other Anti-Inflammatory Agents in the Treatment of Neurodegenerative Disease". Current Alzheimer Research, Jul. 2005, vol. 2, No. 3, pp. 355-365.
Adrianna Z Herskovits et al. "Sirtuin Deacetylases in Neurodegenerative Diseases of Aging". Dell Research, Jun. 2013, vol. 23, No. 6, pp. 746-758.

(Continued)

*Primary Examiner* — Kara R McMillian
(74) *Attorney, Agent, or Firm* — Oliff PLC

(57) ABSTRACT

A method of inhibiting neuroinflammation in neuron surrounding cells, includes a step of treating the neuron surrounding cells with at least one tyrosine kinase inhibitor or sirtuin-2 inhibitor or a combination thereof, to inhibit the neuroinflammation. A method of managing neuroinflammation or neuroinflammation mediated neurodegenerative disease or disorder in a subject in need thereof, includes administering at least one tyrosine kinase inhibitor or sirtuin-2 inhibitor or a combination thereof to the subject. A composition includes at least one tyrosine kinase inhibitor or at least one sirtuin-2 inhibitor optionally along with pharmaceutically acceptable excipient.

6 Claims, 7 Drawing Sheets

(56) References Cited

OTHER PUBLICATIONS

H. Patterson et al. "Protein Kinase Inhibitors in the Treatment of Inflammatory and Autoimmune Diseases". Clinical and Experimental Immunology, Apr. 2014, vol. 176, No. 1, pp. 1-10.
Hong-Qi Yang et al. "Current Advances in the Treatment of Alzheimer's Disease: Focused On Considerations Targeting Aβ And TAU". Translational Neurodegeneration, Oct. 2012, vol. 1, pp. 1-12.

* cited by examiner

METHODS AND COMPOSITIONS FOR MANAGING NEUROINFLAMMATION AND NEURODEGENERATION

TECHNICAL FIELD

The present disclosure relates to the field of biotechnology, medical and cellular biology. In particular, the disclosure relates to methods and compositions for managing neuroinflammation and neuroinflammation mediated neurodegenerative disease or disorder

BACKGROUND OF THE DISCLOSURE

Neurodegeneration, as a collective term, involves the progressive loss of structure or function of neurons, including death of neurons in various areas of the Brain. Neurodegenerative diseases including Parkinson's disease (PD), Alzheimer's disease (AD), Huntington's disease (HD) and Multiple sclerosis (MS) are emerging as a serious challenge to the ageing population. The hallmarks of neurodegeneration or neuronal cell death are oxidative stress, increased protein (α-synuclein/amyloid) aggregates in the neurons and chronic low-level inflammation in the Central Nervous System (CNS).

Parkinson's disease (PD) is a neurodegenerative disease characterized by severe motor symptoms, including rigidity, uncontrollable tremor, postural instability and slowness of movement. The major pathological hallmarks of PD involve neurodegeneration in the Substantia nigra pars compacta resulting in loss of dopaminergic neurons, reduced levels of Dopamine in the Striatum as well as aggregation of alpha-synuclein. It is the second most common neurodegenerative disease, after Alzheimer's disease. The causative agents of this disease may include oxidative stress, genetic mutations, mitochondrial dysfunction and protein misfolding. L-DOPA is the present canonical symptomatic treatment for this disease but it only supplements the dopamine levels until a particular extent. On further progression, there is no treatment providing substantial therapeutic benefit. This treatment also does not cease further neurodegeneration. Although other treatments have been developed in the last 30 years, most patients use L-DOPA in view of its superior efficacy in controlling PD symptoms. Unfortunately, L-DOPA is associated with long-term motor complications (motor fluctuations and dyskinesias). The main causes of these undesirable effects are the narrowing of the therapeutic window with the natural progression of the disease, pulsatile dopaminergic stimulation due to the short half-life of the drug and erratic absorption.

Multiple sclerosis (MS) is a demyelinating disease in which the insulating covers of nerve cells in the brain and spinal cord are damaged. This damage disrupts the ability of parts of the nervous system to communicate, resulting in a range of signs and symptoms, including physical, mental, and sometimes psychiatric problems.

Huntington's disease (HD), also known as Huntington's chorea, is an inherited disorder that results in death of brain cells. The earliest symptoms are often subtle problems with mood or mental abilities. Humans have two copies of the Huntingtin gene (HTT), which codes for the protein Huntingtin (HTT). The gene is also called HD and IT15, which stands for 'interesting transcript 15'. Part of this gene is a repeated section called a trinucleotide repeat, which varies in length between individuals and may change length between generations. If the repeat is present in a healthy gene, a dynamic mutation may increase the repeat count and result in a defective gene. When the length of this repeated section reaches a certain threshold, it produces an altered form of the protein, called mutant Huntingtin protein (mHTT). The differing functions of these proteins are the cause of pathological changes which in turn cause the disease symptoms.

Present therapeutics help only to reduce the symptoms and cures are still not available. Therefore, there is an immediate need to look for therapeutics that can target and ameliorate the conditions presented in such neurodegenerative diseases.

Studies implicate inflammation in neurodegenerative diseases like Parkinson's disease, Alzheimer's disease, Huntington's disease, etc. Contrary to the traditionally held belief that the brain is an immune-privileged site due to the presence of the Blood-Brain Barrier (BBB), recent studies have established that the brain is fully capable of mustering an immune response. Inflammation in the brain does not involve the peripheral immune system and does not involve antibodies or T-Cells. The immune reaction in the brain depends on the synthesis of inflammatory components by Glial cells especially the resident phagocytes, which in the case of the brain, are the microglia.

Within the brain, glial cells play a critical role in maintaining a microenvironment of homeostatis that promotes neuronal survival. Microglia mediate innate immune responses to invading pathogens by secreting a myriad of factors that include, cytokines, chemokines, prostaglandins, reactive oxygen and nitrogen species, and growth factors. Therefore, pro- and anti-inflammatory responses must be tightly regulated to prevent the potential detrimental effects of prolonged inflammation-induced oxidative stress on vulnerable neuronal populations.

In the normal adult brain, microglial cells are usually in the resting state. When activated, these cells are known to release various types of pro-inflammatory molecules such as Nitric Oxide (NO) and cytokines which cause damage and cell death in the surrounding neurons. For instance, in Parkinson's disease, evidence of activated microglia, accumulation of cytokines as well as nuclear factor kappa B (NF-κB) pathway activation has been found to contribute to the progression of PD.

Presently, the options for treating neuroinflammation and neurodegenerative diseases or disorders are limited. The instant disclosure therefore provides for methods and compositions which address the limitations existing in the prior art.

SUMMARY OF THE DISCLOSURE

The present disclosure relates to a method of managing a neurodegenerative disease or disorder in a subject in need thereof, comprising administering at least one compound capable of inhibiting or modulating inflammation in the subject, for managing the neurodegenerative disease or disorder; a composition for managing a neurodegenerative disease or disorder in a subject in need thereof, comprising at least one compound capable of inhibiting or modulating inflammation, optionally along with pharmaceutically acceptable excipient; a method of inhibiting neurodegeneration induced by inflammation in neuron surrounding cells, comprising step of treating the neuron surrounding cells with at least one compound capable of inhibiting or modulating inflammation, to inhibit the neurodegeneration; a method of inhibiting neuroinflammation in neuron surrounding cells, comprising step of treating the neuron surrounding cells with at least one tyrosine kinase inhibitor or sirtuin-2 inhibitor or a combination thereof, to inhibit the neuroinflammation; a method of managing neuroinflammation or neuroinflammation mediated neurodegenerative disease or disorder in a subject in need thereof, comprising administering at least one tyrosine kinase inhibitor or sirtuin-2 inhibitor or a combination thereof to the subject; and a composition for managing neuroinflammation or neuroinflammation mediated neurodegenerative disease or disorder in a subject in need thereof, comprising at least one tyrosine kinase inhibitor or sirtuin-2 inhibitor or a combination thereof, optionally along with pharmaceutically acceptable excipient.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure where:

DETAILED DESCRIPTION OF THE DISCLOSURE

Figure 1:
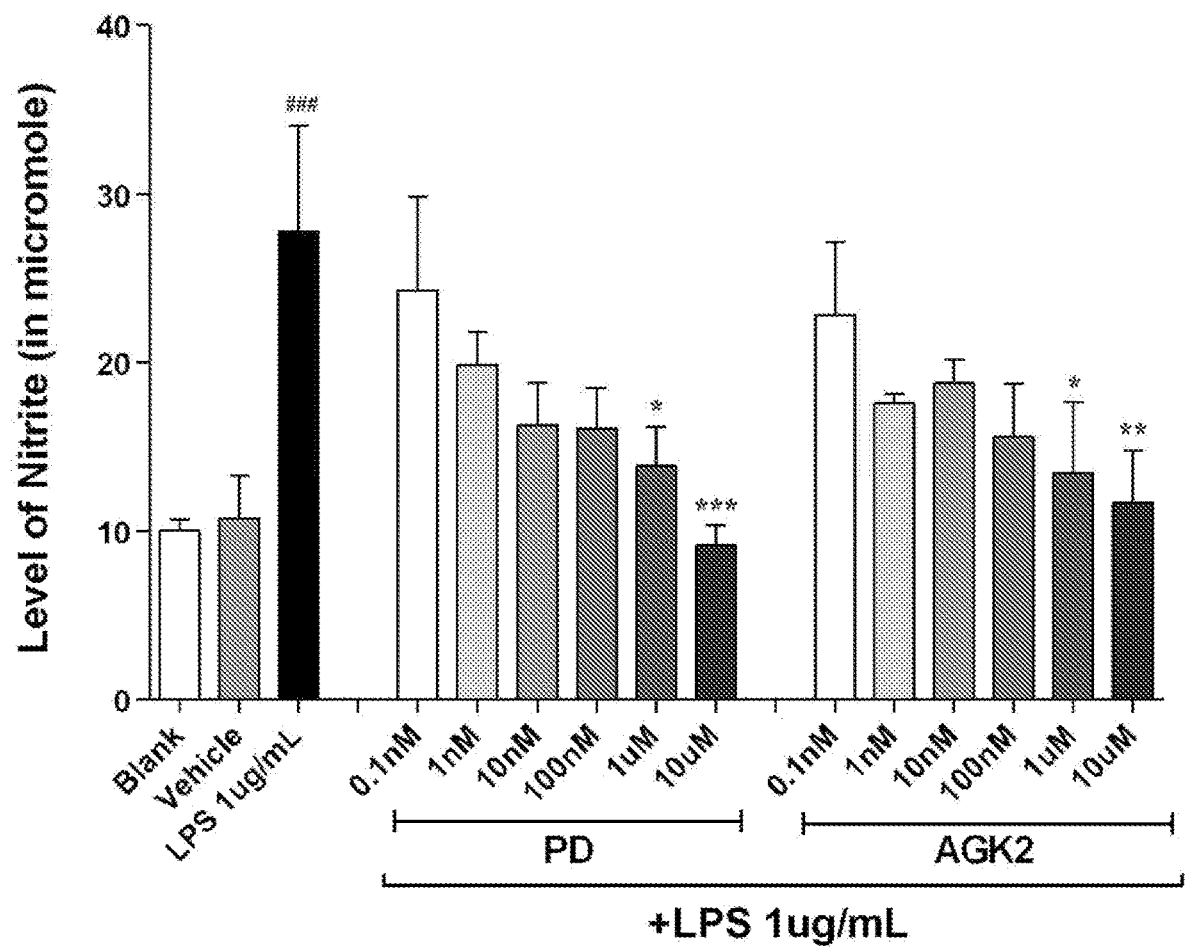
FIG. 1 depicts anti-inflammatory response of compounds PD180970 and AGK2 on LPS induced nitrite release in BV2 cell line.

The present disclosure relates to a method of managing a neurodegenerative disease or disorder in a subject in need thereof, comprising administering at least one compound capable of inhibiting or modulating inflammation in the subject, for managing the neurodegenerative disease or disorder.

The present disclosure also relates to a composition for managing a neurodegenerative disease or disorder in a subject in need thereof, comprising at least one compound capable of inhibiting or modulating inflammation, optionally along with pharmaceutically acceptable excipient.

The present disclosure also relates to a method of inhibiting neurodegeneration induced by inflammation in neuron surrounding cells, comprising step of treating the neuron surrounding cells with at least one compound capable of inhibiting or modulating inflammation, to inhibit the neurodegeneration.

In an embodiment, the compound is selected from the group comprising Non-steroidal Anti-inflammatory Drug, Anti-inflammatory molecule, Tyrosine Kinase Inhibitor, Sirtuin-2 Inhibitor, or any combination thereof.

In another embodiment, the compound is Tyrosine Kinase Inhibitor.

In an embodiment, the tyrosine kinase inhibitor is a molecule or a compound from tyrosine kinase inhibitor family.

In yet another embodiment, the compound is Sirtuin-2 Inhibitor.

In an embodiment, wherein the sirtuin-2 inhibitor is a molecule or a compound from Sirtuin-2 inhibitor family.

In still another embodiment, the Non-steroidal Anti-inflammatory Drug is selected from the group comprising Celecoxib, Valdecoxib, Rofecoxib, Diclofenac, Diflunisal, Etodolac, Fenoprofen, Flurbiprofen, Ibuprofen, Indomethacin, Ketoprofen, Ketorolac, Mefenamic Acid, Meloxicam, Nabumetone, Naproxen, Oxaprozin, Piroxicam, Sulindac and Tolmetin; the Anti-inflammatory molecule is NAC; the Tyrosine Kinase Inhibitor is selected from the group comprising PD180970, Axitinib, Bortezomib, Bosutinib, Cabozantinib, Carfilzomib, Crizotinib, Dabrafenib, Dasatinib, Erlotinib, Gefitinib, Ibrutinib, Idelalisib, Imatinib, Lapatinib, Nilotinib, Palbociclib, Pazopanib, Pegaptanib, Ponatinib, Regorafenib, Ruxolitinib, Sorafenib, Sunitinib, Tofacitinib, Trametinib, Vandetanib, Vemurafenib and Vismodegib; and the Sirtuin-2 Inhibitor is selected from AGK-2 and AK-7; or any combination thereof.

The present disclosure relates to a method of inhibiting neuroinflammation in neuron surrounding cells, comprising step of treating the neuron surrounding cells with at least one tyrosine kinase inhibitor or sirtuin-2 inhibitor or a combination thereof, to inhibit the neuroinflammation.

The present disclosure also relates to a method of managing neuroinflammation or neuroinflammation mediated neurodegenerative disease or disorder in a subject in need thereof, comprising administering at least one tyrosine kinase inhibitor or sirtuin-2 inhibitor or a combination thereof to the subject.

The present disclosure also relates to a composition for managing neuroinflammation or neuroinflammation mediated neurodegenerative disease or disorder in a subject in need thereof, comprising at least one tyrosine kinase inhibitor or sirtuin-2 inhibitor or a combination thereof, optionally along with pharmaceutically acceptable excipient.

In an embodiment, the tyrosine kinase inhibitor is a molecule or a compound from tyrosine kinase inhibitor family.

In another embodiment, the tyrosine kinase inhibitor is selected from the group comprising PD180970, Axitinib, Bortezomib, Bosutinib, Cabozantinib, Carfilzomib, Crizotinib, Dabrafenib, Dasatinib, Erlotinib, Gefitinib, Ibrutinib, Idelalisib, Imatinib, Lapatinib, Nilotinib, Palbociclib, Pazopanib, Pegaptanib, Ponatinib, Regorafenib, Ruxolitinib, Sorafenib, Sunitinib, Tofacitinib, Trametinib, Vandetanib, Vemurafenib, Vismodegib, their stereoisomer, pharmaceutically acceptable salt, polymorph, solvate, hydrate, or any combination thereof.

In yet another embodiment, the sirtuin-2 inhibitor is a molecule or a compound from Sirtuin-2 inhibitor family.

In still another embodiment, the sirtuin-2 inhibitor is selected from the group comprising AGK-2, AK-7, their stereoisomer, pharmaceutically acceptable salt, polymorph, solvate, hydrate, or any combination thereof.

In still another embodiment, the compound is administered along with a pharmaceutically acceptable excipient.

In still another embodiment, the inhibitor is administered along with a pharmaceutically acceptable excipient.

In still another embodiment, the pharmaceutically acceptable excipient is selected from the group comprising to granulating agent, binding agent, lubricating agent, disintegrating agent, sweetening agent, glidant, anti-adherent, anti-static agent, surfactant, anti-oxidant, gum, coating agent, coloring agent, flavouring agent, additive, solvent, viscosity enhancer, plasticizer, preservative, suspending agent, emulsifying agent, plant cellulosic material, spheronization agents and combinations thereof.

In still another embodiment, the subject is mammal, preferably human.

In still another embodiment, the neurodegeneration disease or disorder is selected from the group comprising Parkinson's disease, Alzheimer's disease, Huntington's disease, multiple sclerosis and amyotrophic lateral sclerosis.

In still another embodiment, the inhibitor stops neuronal death induced by inflammation in neuron surrounding cells.

In still another embodiment, the neuron surrounding cells is selected from the group comprising glial cells, astrocytes and immune cells or any combination thereof.

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular as is considered appropriate to the context and/or application. The various singular/plural permutations may be expressly set forth herein for the sake of clarity. Generally, nomenclatures used in connection with, and techniques of biotechnology, medical and cellular biology described herein are those well-known and commonly used in the art. In case of conflict, the present specification, including definitions, will control. The materials, methods, figures and examples are illustrative only and not intended to be limiting.

As used herein, the term "managing" or "management" includes treating or healing of a disease condition or disorder or ill effects or side effects. The term also encompasses maintenance of the optimum state and prevention of the further progress in the disease condition or disorder or ill effects or side effects. Further, "management" or "managing" refers to decreasing the risk of death due to a disease or disorder, delaying the onset of a disease or disorder, inhibiting the progression of a disease or disorder, partial or complete cure of a disease or disorder and/or adverse effect attributable to the said disease or disorder, obtaining a desired pharmacologic and/or physiologic effect (the effect may be prophylactic in terms of completely or partially preventing a disorder or disease or condition, or a symptom thereof and/or may be therapeutic in terms of a partial or complete cure for a disease or disorder and/or adverse effect attributable to the disease or disorder), or relieving a disease or disorder (i.e. causing regression of the disease or disorder).

As used herein, the term "neuroinflammation" includes inflammation of the nervous tissue or neuronal surrounding cells. The neuroinflammation may be initiated in response to a variety of cues, including infection, traumatic brain injury, toxic metabolites, autoimmunity, etc.

As used herein, the term "neurodegeneration" includes progressive loss of structure or function of neurons, including death of neurons. The neurodegenerative disease or disorder of the present disclosure includes but is not limited to amyotrophic lateral sclerosis, multiple sclerosis, Parkinson's, Alzheimer's, and Huntington's which occur as a result of neurodegenerative processes.

As used herein, the term "neuronal surrounding cells" includes any cell that surrounds neuron(s). The neuronal surrounding cells of the present disclosure include but are not limited to glial cells, astrocytes, immune cells, etc. Throughout the present disclosure, the terms "glial cells" and "microglia" are used interchangeably and have the same meaning and scope.

As used herein, the terms "compound" and "anti-inflammatory compound" are used interchangeably and include any compound that is capable of inhibiting or modulating inflammation, including but not limiting to prior known anti-inflammatory compound. Such compound includes but is not limited to Nonsteroidal anti-inflammatory drugs (NSAIDs), anti-inflammatory molecule, Tyrosine Kinase Inhibitor, Sirtuin-2 Inhibitor, etc.

As used herein, the term "Tyrosine Kinase inhibitor" (TKI) includes any compound that inhibits the enzyme tyrosine kinases.

As used herein, the term "Sirtuin-2 inhibitor" includes any compound that inhibits the enzyme Sirtuin-2 (SIRT2).

Throughout the present disclosure, the terms "CCND-01", "ND1" and "PD180790" are used interchangeably and have the same meaning and scope.

Throughout the present disclosure, the terms "CCND-02", "ND2", "AGK2" and "AGK-2" are used interchangeably and have the same meaning and scope.

As used herein, the term "cryopreservation solution" means a composition/solution used for preservation of cells for longer duration/shelf life. In an embodiment of the present disclosure, the cryoprotectant solution per 500 mL comprises 150 mL of glycerol, 150 mL of ethylene glycol and 200 ml of 1×PBS, adjusted to pH to 7.4. On requirement, the cryopreserved cells are thawed and used as per the requirement.

The present disclosure relates to use of a compound capable of managing neuroinflammation for management of neurodegenerative disease or disorder.

Particularly, the present disclosure relates to use of a compound capable of managing neuroinflammation for treatment or prevention of neuroinflammation mediated neurodegenerative disease or disorder.

In an embodiment, the compound capable of managing neuroinflammation is selected from group comprising but not limiting to Tyrosine Kinase Inhibitor, Sirtuin-2 inhibitor, Anti-inflammatory molecule, NSAID or any combination thereof.

The present disclosure relates to use of NAC alone or in combination with any other anti-inflammatory compound for managing neuroinflammation mediated neurodegenerative disease or disorder.

The present disclosure relates to use of Tyrosine Kinase Inhibitor and/or Sirtuin-2 inhibitor for managing neuroinflammation or neuroinflammation mediated neurodegenerative disease or disorder.

In an embodiment, the present disclosure relates to use of anti-inflammatory compound for inhibiting, treating or preventing neuroinflammation mediated neurodegenerative disease or disorder.

In an embodiment, the present disclosure relates to use of NAC for inhibiting, treating or preventing neuroinflammation mediated neurodegenerative disease or disorder.

In an embodiment, the present disclosure relates to use of Tyrosine Kinase Inhibitor for inhibiting, treating or preventing neuroinflammation or neuroinflammation mediated neurodegenerative disease or disorder.

In an embodiment, the present disclosure relates to use of Sirtuin-2 inhibitor for inhibiting, treating or preventing neuroinflammation or neuroinflammation mediated neurodegenerative disease or disorder.

In an embodiment, the present disclosure relates to use of compounds selected from a group comprising Tyrosine Kinase Inhibitor, Sirtuin-2 inhibitor, Anti-inflammatory molecule, NSAID or a combination thereof, along with one or more compound capable of inhibiting inflammation or neuroinflammation, for inhibiting, treating or preventing neuroinflammation mediated neurodegenerative disease or disorder.

The present disclosure relates to prophylactic or therapeutic use of any compound within the family of Tyrosine Kinase Inhibitors and/or Sirtuin-2 Inhibitors, or their stereoisomers, pharmaceutically acceptable salts, polymorphs, solvates and hydrates thereof, for preventing or treating neuroinflammation and neurodegeneration induced by neuroinflammation, in a subject in need thereof.

The present disclosure also relates to a method of managing neurodegenerative disease or disorder in a subject in need thereof, said method comprising act of administering an effective amount of at least one anti-inflammatory compound, or a composition comprising the anti-inflammatory compound, to the subject for managing the neurodegenerative disease or disorder. In an embodiment, the anti-inflammatory compound comprises any compound capable of treating, inhibiting, preventing or reducing inflammation.

In an embodiment, the present disclosure also relates to a method of managing neuroinflammation mediated neurodegenerative disease or disorder in a subject in need thereof, said method comprising act of administering an effective amount of at least one anti-inflammatory compound, or a composition comprising the anti-inflammatory compound, to the subject for managing the neurodegenerative disease or disorder.

The present disclosure also relates to a method of managing neuroinflammation or neuroinflammation mediated neurodegenerative disease or disorder in a subject in need thereof, said method comprising act of administering to the subject an effective amount of at least one compound, or a composition comprising the compound, selected from Tyrosine Kinase Inhibitor, Sirtuin-2 inhibitor or a combination of Tyrosine Kinase Inhibitor and Sirtuin-2 inhibitor, for ameliorating the neurodegenerative disease or disorder.

In an embodiment, the present disclosure relates to a method of managing neuroinflammation, including neuroinflammation of neuronal surrounding cells, in a subject in need thereof, said method comprising administering at least one Tyrosine Kinase Inhibitor and/or a Sirtuin-2 inhibitor or their stereoisomers, pharmaceutically acceptable salts, polymorphs, solvates and hydrates thereof, to the subject.

In another embodiment, the present disclosure relates to a method of managing a neurodegenerative disease or disorder in a subject in need thereof, said method comprising comprises the step of administering at least one anti-inflammatory compound or its stereoisomer, pharmaceutically acceptable salt, polymorph, solvate and hydrate thereof, to the subject to manage the neurodegenerative disease or disorder.

In another embodiment, the present disclosure relates to a method of managing a neurodegenerative disease or disorder in a subject in need thereof, said method comprising comprises the step of administering at least one compound selected from Anti-inflammatory molecule, NSAID, Tyrosine Kinase Inhibitor and/or Sirtuin-2 inhibitor or their stereoisomers, pharmaceutically acceptable salts, polymorphs, solvates and hydrates thereof, to the subject.

In an embodiment, the method of treating neuroinflammation mediated neurodegeneration in a subject in need thereof as per the present disclosure, comprises the steps of: administering a pharmaceutical/therapeutic composition comprising an effective amount of at least one compound having anti-inflammatory activity or their stereoisomers, pharmaceutically acceptable salts, polymorphs, solvates and hydrates thereof, to the subject, for ameliorating the neurodegeneration.

In an embodiment, the method of treating neuroinflammation mediated neurodegeneration in a subject in need thereof as per the present disclosure, comprises the steps of: administering a pharmaceutical/therapeutic composition comprising an effective amount of at least one Anti-inflammatory molecule, NSAID, Tyrosine Kinase Inhibitor compound and/or a Sirtuin-2 inhibitor compound or their stereoisomers, pharmaceutically acceptable salts, polymorphs, solvates and hydrates thereof, to the subject, for ameliorating the neurodegeneration.

In an embodiment, the method of preventing neuroinflammation mediated neurodegeneration in a subject in need thereof as per the present disclosure, comprises the act of administering to a neurodegeneration high risk subject a prophylactically effective amount of at least one anti-inflammatory compound or their stereoisomers, pharmaceutically acceptable salts, polymorphs, solvates and hydrates thereof or a composition comprising the said compound optionally along with a pharmaceutically acceptable excipient.

In an embodiment, the method of preventing neuroinflammation mediated neurodegeneration in a subject in need thereof as per the present disclosure, comprises the act of administering to a neurodegeneration high risk subject a prophylactically effective amount of at least one compound within the family of Anti-inflammatory molecule, NSAID, Tyrosine Kinase Inhibitors and/or a Sirtuin-2 inhibitor or their stereoisomers, pharmaceutically acceptable salts, polymorphs, solvates and hydrates thereof or a composition comprising the said compound optionally along with a pharmaceutically acceptable excipient.

The method of inhibiting, treating or preventing neurodegeneration in a subject where the neurodegeneration is induced by neuroinflammation (which includes inflammation of neuronal surrounding cells), said method comprises the act of administering an effective amount of one or more anti-inflammatory compound, or a composition comprising one or more anti-inflammatory compound, or their stereoisomers, pharmaceutically acceptable salts, polymorphs, solvates and hydrates thereof.

The method of inhibiting, treating or preventing neurodegeneration in a subject where the neurodegeneration is induced by neuroinflammation (which includes inflammation of neuronal surrounding cells), said method comprises the act of administering an effective amount of a compound, or a composition comprising the compound, selected from the group comprising Anti-inflammatory molecule, NSAID, Tyrosine Kinase Inhibitor and/or Sirtuin-2 Inhibitor or their stereoisomers, pharmaceutically acceptable salts, polymorphs, solvates and hydrates thereof.

In a non-limiting embodiment of the present disclosure, the combined effect of Tyrosine Kinase Inhibitor and Sirtuin-2 Inhibitor for managing neuroinflammation and neuroinflammation mediated neurodegeneration is greater than the sum of their separate effects.

In embodiments of the present disclosure, compound from the family of Tyrosine Kinase Inhibitor or Sirtuin-2 inhibitor is optionally combined with one or more anti-inflammatory compound from a different family.

In embodiments of the present disclosure, the neurodegeneration disease or disorder is selected from a group comprising Parkinson's disease, Alzheimer's disease, Huntington's disease, Multiple Sclerosis and amyotrophic lateral sclerosis.

In an embodiment of the present disclosure, neuroinflammation includes inflammation of neuronal surrounding cells such as glial cells, astrocytes, immune cells, etc.

In embodiments of the present disclosure, the neurodegenerative disease or disorder includes any disease or disorder caused by chronic or acute levels of inflammation and inflammatory markers surrounding neurons compared to normal state, and is selected from the group comprising Parkinson's disease, Alzheimer's disease, Huntington's disease, multiple sclerosis and amyotrophic lateral sclerosis.

In an embodiment, the methods and compositions of the present disclosure provide for managing multiple neurological or neurodegenerative disorders.

The present disclosure also relates to a method of inhibiting neuroinflammation in neuron surrounding cells, comprising step of treating the neuron surrounding cells with at least one Tyrosine Kinase Inhibitor or Sirtuin-2 inhibitor or a combination thereof, to inhibit the neuroinflammation.

In an embodiment, the present disclosure relates to a method of inhibiting neuroinflammation in neuron surrounding cells such as but not limiting to glial cells, comprising step of treating the neuron surrounding cells with at least one Tyrosine Kinase Inhibitor and/or sirtuin-2 inhibitor to inhibit the neuroinflammation.

The present disclosure also relates to a method of inhibiting neurodegeneration induced by inflammation in neuron surrounding cells, comprising step of treating the neuron surrounding cells with at least one anti-inflammatory compound.

The present disclosure also relates to a method of inhibiting neurodegeneration induced by inflammation in neuron surrounding cells, comprising step of treating the neuron surrounding cells with at least one Tyrosine Kinase Inhibitor and/or Sirtuin-2 to inhibit the neurodegeneration.

In an embodiment, the present disclosure relates to a method of inhibiting neurodegeneration induced by inflammation in neuron surrounding cells such as but not limiting to glial cells, comprising step of treating the neuron surrounding cells with at least one Tyrosine Kinase Inhibitor and/or Sirtuin-2 inhibitor to stop neuronal death induced by inflammation in the neuron surrounding cells.

In embodiments of the present disclosure, the compound (s) of the present disclosure is selected from a group comprising but not limiting to NSAID such as COX-2 Selective Non-steroidal Anti-inflammatory Drugs (NSAIDs), Non-selective NSAIDs; Anti-inflammatory molecule; Tyrosine Kinase Inhibitor; Sirtuin-2 Inhibitor; or any combination thereof.

In an exemplary embodiment of the present disclosure, the COX-2 NSAID is selected from a group comprising but not limiting to Celecoxib, Valdecoxib and Rofecoxib or any combination thereof.

In an exemplary embodiment of the present disclosure, the non-selective NSAID is selected from a group comprising but not limiting to Diclofenac, Diflunisal, Etodolac, Fenoprofen, Flurbiprofen, Ibuprofen, Indomethacin, Ketoprofen, Ketorolac, Mefenamic Acid, Meloxicam, Nabumetone, Naproxen, Oxaprozin, Piroxicam, Sulindac and Tolmetin or any combination thereof.

In an exemplary embodiment, the Anti-inflammatory molecule is but not limited to N-acetylcysteine (NAC). NAC is a powerful antioxidant and a scavenger of hydroxyl radicals. NAC, a thiol containing amino acid, and a precursor for glutathione (GSH) synthesis. NAC acts as a scavenger of free radicals due to its direct interaction with ROS. In an embodiment, the present disclosure relates to use of N-acetylcysteine or compositions comprising N-acetylcysteine for managing neuroinflammation mediated neurodegeneration.

Tyrosine Kinase Inhibitor compounds stop neuronal death induced by inflammation in neuron surrounding cells including but not restricted to glial cells, astrocytes and immune cells, by inhibiting tyrosine kinases.

In all embodiments of the present disclosure, the Tyrosine Kinase Inhibitor includes any molecule or compound belonging to the Tyrosine Kinase Inhibitor family.

In an exemplary embodiment of the present disclosure, the Tyrosine Kinase Inhibitor is selected from the group comprising but not limiting to PD180790, Axitinib, Bortezomib, Bosutinib, Cabozantinib, Carfilzomib, Crizotinib, Dabrafenib, Dasatinib, Erlotinib, Gefitinib, Ibrutinib, Idelalisib, Imatinib, Lapatinib, Nilotinib, Palbociclib, Pazopanib, Pegaptanib, Ponatinib, Regorafenib, Ruxolitinib, Sorafenib, Sunitinib, Tofacitinib, Trametinib, Vandetanib, Vemurafenib, Vismodegib, their stereoisomers, pharmaceutically acceptable salts, polymorphs, solvates, hydrates, or any combination thereof.

Sirtuins are protein deacetylases, which represent a new class of histone deacetylases (HDAC) involved in gene silencing. SIRT modulators are potential therapeutics for cancer, diabetes, muscle differentiation, heart failure, neurodegeneration, and aging. Sirtuin-2 Inhibitor compounds stop neuronal death induced by inflammation in neuron surrounding cells including but not restricted to glial cells, astrocytes and immune cells or any combination thereof, by inhibiting Sirtuin-2.

In all embodiments of the present disclosure, the sirtuin-2 Inhibitor includes any molecule or compound belonging to the sirtuin-2 Inhibitor family.

In an exemplary embodiment of the present disclosure, the sirtuin-2 inhibitor is selected from the group comprising but not limiting to AK-7, AGK-2, their stereoisomers, pharmaceutically acceptable salts, polymorphs, solvates, hydrates, or any combination thereof.

The present disclosure also relates to a composition for managing neuroinflammation in a subject in need thereof, comprising at least one tyrosine kinase inhibitor or sirtuin-2 inhibitor or a combination thereof, optionally along with pharmaceutically acceptable excipient.

The present disclosure also relates to a composition for managing a neuroinflammation mediated neurodegenerative disease or disorder in a subject in need thereof, comprising at least one anti-inflammatory compound, optionally along with pharmaceutically acceptable excipient.

The present disclosure also relates to a composition for managing a neuroinflammation mediated neurodegenerative disease or disorder in a subject in need thereof, comprising at least one tyrosine kinase inhibitor or sirtuin-2 inhibitor or a combination thereof, optionally along with pharmaceutically acceptable excipient.

In all embodiments of the present disclosure, the subject is mammal, preferably human.

In addition to the active ingredients, the compositions of the present disclosure may contain suitable pharmaceutically-acceptable excipients which facilitate processing of the active compounds into preparations which can be used pharmaceutically. The term "excipient" includes an inert substance used as vehicle/carrier and/or diluent for the active ingredient. The term "excipient" also includes a substance added to a formulation/composition to provide benefit of the processing or cryo-protection of active ingredient and is intended to be present in the final product as an inactive ingredient. Further details on techniques for formulation and administration may be found in the latest edition of Remington's Pharmaceutical Sciences.

In an exemplary embodiment of the present disclosure, the pharmaceutically acceptable excipient is selected from group comprising but not limiting to granulating agent, binding agent, lubricating agent, disintegrating agent, sweetening agent, glidant, anti-adherent, anti-static agent, surfactant, anti-oxidant, gum, coating agent, coloring agent, flavouring agent, additive, solvent, viscosity enhancer, plasticizer, preservative, suspending agent, emulsifying agent, plant cellulosic material, spheronization agents and combinations thereof.

In another exemplary embodiment of the present disclosure, the composition is formulated into dosage form selected from group comprising solid oral formulation, liquid formulation and parenteral formulation or any combinations thereof. Controlled as well as prolonged release formulation are contemplated.

In still another exemplary embodiment of the present disclosure, the solid oral formulation is selected from group comprising tablet, capsule, troche, lozenge, dispersible powder, dispersible granule or any combinations thereof; the liquid formulation is selected from group comprising aqueous or oily suspension, emulsion, drop, emulsion in hard or soft gel capsule, syrup, elixir or any combinations thereof; and the parenteral formulation is selected from group comprising intravenous injection, intramuscular injection, intraperitoneal injection, intramuscular depot, subcutaneous injection, percutaneous injection or any combinations thereof.

In an embodiment, the composition of the present disclosure is administered through modes selected from the group comprising intraperitoneal administration, oral administration, intramuscular administration, intravenous administration, intra articular administration, intradermal administration or injection in any other appropriate part or any combination thereof.

Depending on the route of administration, different excipient/carrier is used for the instant composition. Those skilled in art will know to choose a suitable formulation and dosage of the composition of the present disclosure for managing neuroinflammation or neuroinflammation mediated neurodegenerative disease or disorder.

As used herein, the term "effective amount" includes the amount of active ingredient (i.e. TKI, Sirtuin-2 inhibitor or a combination thereof), required for managing neuroinflammation, any condition, disease or disorder arising due to neuroinflammation; or neuroinflammation mediated neurodegenerative disease or disorder.

In an embodiment of the present disclosure, concentration of the compound(s) for inhibiting neuroinflammation or neuroinflammation mediated neurodegeneration is ranging from about 1 pM to 100 mM, preferably about 1 pM to 10 µM, more preferably about 1 nM to 10 µM.

In an embodiment of the present disclosure, dosage of the compound(s) for managing neuroinflammation or neuroinflammation mediated neurodegeneration is ranging from about 10 mg to 1000 mg.

In an embodiment of the present disclosure, the safe and efficacy drug dose is estimated by preclinical study.

The Central Nervous System (CNS) has different cell types, majority of which are the neurons, glial cells and astrocytes. A complex interaction between the neurons and cells in the vicinity play a major role in progression or reduction of neuronal degeneration/death. Role of Glial cells in inducing chronic inflammation in the CNS has also been implicated in several neurodegenerative diseases including PD, AD and MS. The immune reaction in the brain depends on the synthesis of pro-inflammatory molecules such as Nitric Oxide (NO) and cytokines by Glial cells, which causes damage and cell death in the surrounding neurons. Therefore, in order to mimic the physiology of CNS and study the effect of compounds on the overall physiology of the CNS, the present disclosure employs a neuron-microglia co-culture model which shows Neuroinflammation mediated neuronal toxicity and provides for the activity of test compounds in alleviation of the same.

Neuron-Microglia Co-Culture:

Neuron cells selected from the group comprising but not limiting to mouse brain Cortex neuron, Hippocampal neuron, striatum neuron and 7PA2 are co-cultured with Glial cells in Corning HTS Transwell Plates, the neuron cells in the lower well of the plates and glial cells in the porous permeable support inserted on top of the well. The neuron cells are treated with LPS about 1 ng/ml to 10 g/ml 1 µg/ml in the presence and absence of compound such as but not limiting to NAC, Tyrosine Kinase Inhibitor or Sirt-2 inhibitor and incubated for a duration of about 12 to 72 hours. The survival of the neural cells is then measured using MTS Assay. After about 30 hours, the treatment Media is collected from all conditions and tested for concentration of Nitric oxide using the Griess Assay as well as for cytokine profile using Luminex multiplexing assay.

The present invention discloses the role of anti-inflammatory compounds succha s but not limiting to NAC, Tyrosine Kinase Inhibitors and Sirtuin-2 inhibitors for protection against neurodegeneration in a co-culture model on neurodegeneration upon neuro-inflammation. The inflammation, i.e. release of inflammatory molecules, caused neuronal toxicity, and when the said compounds were introduced in this assay, these compounds, prevent/reduce neuroinflammation and hence, rescue the neuroinflammation mediated neurodegeneration thereby contributing to neuroprotection in neurodegenerative and associated diseases. In an embodiment, treatment with anti-inflammatory compounds causes significant decrease in the activation and inflammatory response of neuron surrounding cells such as glial cells. In an exemplary embodiment of the present disclosure, treatment with anti-inflammatory compounds such as NAC, PD180790 and AGK-2 causes significant decrease in the activation and inflammatory response of neuron surrounding cells, and stops, inhibits or prevents neuronal death induced by inflammation in neuron surrounding cells.

The present invention discloses the role of Tyrosine Kinase Inhibitors and Sirtuin-2 inhibitors for protection against neurodegeneration in a co-culture model on neurodegeneration upon neuro-inflammation. The inflammation, i.e. release of inflammatory molecules, caused neuronal toxicity, and when the said compounds were introduced in this assay, these two compounds, prevent/reduce neuroinflammation and hence, rescue the neuroinflammation mediated neurodegeneration thereby contributing to neuroprotection in neurodegenerative and associated diseases.

Treatment with inhibitors of Tyrosine Kinase and/or Sirtuin-2 cause significant decrease in the activation and inflammatory response of glial cells. While Tyrosine Kinase Inhibitors inhibit p210 Bcr-Abl tyrosine kinase and Sirtuin-2 Inhibitors inhibit SIRT2, the present disclosure employs the same as modulators of neuroinflammation in a microglial cell line model.

In an embodiment of the present disclosure, treatment with PD180790 and AGK-2 causes significant decrease in the activation and inflammatory response of BV2 cells in the LPS neuroinflammation model. While PD180970 and AGK2 are well-characterized and potent inhibitors of p210 Bcr-Abl tyrosine kinase and SIRT2 respectively, the present disclosure investigates their efficacy as modulators of neuroinflammation in a microglial cell line model.

In an embodiment, the present disclosure employs cell lines selected from a group comprising neuronal cells such as but not limiting to N27, and glial cells such as but not limiting to BV2.

N27 neuronal cells are used as cellular model for studying neurodegenerative mechanisms in PD. N27 is a immortalized rat mesencephalic dopaminergic neuronal cell line, developed from the ventral mesencephalon, a region of the brain that is directly affected in PD. N27 cells represent a homogenous population of tyrosine hydroxylase-positive (TH+) neurons with functional characteristics including dopamine synthesis and cellular signaling pathways.

BV-2 cells are retroviral immortalized microglia derived from primary mouse microglia cells. Microglial cells are the dominant immune cells of the brain, which are of monocytic lineage, and function similarly to the macrophages of the systemic immune system. The activity of microglia is closely associated with neural activity, neurodegeneration and infection. The BV-2 cells have morphological, phenotypic and functional markers of macrophages. Microglia have been implicated in several neurological and psychological diseases (e.g., schizophrenia, substance abuse, depression, Alzheimer's disease, Huntington's Chorea, etc) and they express a large variety and number of neurotransmitter receptors which makes them a relevant model for investigating the effects of psychoactive compounds on brain.

In an embodiment of the present disclosure, it is found that Tyrosine Kinase Inhibitor and Sirtuin-2 inhibitor have no neuroprotective effect on neuronal degeneration induced due to oxidative stress inducers such as Hydrogen Peroxide and $MPP^+$, but has a significant Neuroprotective effect in a neuroinflammation mediated neurodegeneration.

In normal physiological condition, superoxide anion (02) is produced as a by-product of mitochondrial respiration. It's limited toxic effects, can either react with nitric oxide to form peroxinitrite anions, which are highly cytotoxic, or dismutate into hydrogen peroxide ($H_2O_2$), a reaction that is accelerated by superoxide dismutase. $H_2O_2$ in turn exerts its toxic effects mainly through the ferrous ion-dependent formation of the highly reactive hydroxyl radical ($OH^-$). In the $H_2O_2$ model, treatment of N27 cells with hydrogen peroxide increases the production of $OH^-$ ions which leads to alterations of lipids, proteins, and DNA resulting in cell death. MPTP (1-methyl-4-phenyl-1,2,3,6-tetrahydropyridine) is a contaminant commonly found in illegal narcotics. It is capable of crossing the blood brain barrier (BBB) and gets metabolized into highly toxic MPP+(1-methyl-4-phenylpyridinium) by monoamine oxidase B in glial cells. MPP+ is transported into the dopaminergic neurons by the dopamine transporter (DAT) and accumulates in the mitochondria, resulting in ATP depletion through inhibition of complex I activity, inactivation of mitochondrial aconitase causing accumulation of labile iron in the neurons, altered mitochondrial membrane potential, increased reactive oxygen species (ROS), and finally apoptotic cell death.

In an embodiment, the present disclosure employs Lipopolysaccharide (LPS) induced neurodegeneration model to study microglia activation in in-vitro condition. LP S is a major component of the outer cell wall of Gram-negative bacteria and is an established activator of microglia. Recognized by Toll-like receptor (TLR)-4 expressed on microglia, LPS triggers the activation of a cascade of enzymes and transcription factors, including nuclear transcription factor kappa B (NF-κB) and mitogen-activated protein kinases (MAPKs), such as p38 MAP kinase, extracellular signal-regulated kinase (ERK), and c-Jun N-terminal kinase (JNK). This results in the release of numerous pro-inflammatory mediators such as NO, TNF-α, IL-1β and IL-6 which creates an inflammatory micro-environment and results in neuronal cell death. LPS-stimulated microglia has become a commonly used model.

In an embodiment of the present disclosure, SIRT2 inhibitor suppresses inflammatory responses in mice through p65 deacetylation and inhibition of NF-κB activity. SIRT2 is responsible for the deacetylation and activation of G6PD, stimulating pentose phosphate pathway to supply cytosolic NADPH to counteract oxidative damage and protect mouse erythrocytes.

IL-6 is a proinflammatory cytokine released from immune cells like microglia, IL-6 in turn leads to aggravated cell stress and death, adding to neurodegeneration. Reduction in IL-6 ameliorates neuronal survival.

Tyrosine Kinase Inhibitor, NAC and Sirtuin-2 Inhibitor exhibit neuroprotective effect, inhibiting/treating/preventing neuronal death or degeneration induced by neuroinflammatory conditions such as increased nitrite release, IL-6 secretion, MCP-1 secretion and nF-κB activity.

In some embodiments, the present disclosure also relates to the following aspects:
  I. A method for treating a subject, comprising the steps of
     a. Providing a subject, wherein a subject has a neurodegenerative disease; b. administering to a Neurodegeneration affected subject a therapeutic composition comprising at least one Tyrosine Kinase Inhibitor compound or a Sirtuin 2 inhibitor compound or their stereoisomers, pharmaceutically acceptable salts, polymorphs, solvates and hydrates thereof under such conditions such that said neurodegenerative disease is ameliorated.
  II. A method for preventing Neurodegeneration in a subject in need thereof comprising: administering to a Neurodegeneration high risk subject a relevant dose of a compound within family of Tyrosine Kinase Inhibitors or a Sirtuin 2 inhibitor compound or their stereoisomers, pharmaceutically acceptable salts, polymorphs, solvates and hydrates thereof.

III. A method of treating or preventing neurodegeneration in a subject where neurodegeneration is induced by neuroinflammation comprising: administering to a subject a prophylactically effective amount of a compound selected from a group of Tyrosine Kinase Inhibitor compounds or their stereoisomers, pharmaceutically acceptable salts, polymorphs, solvates and hydrates thereof.

IV. The method of aspect III, wherein the said inhibitor compounds stops neuronal death induced by inflammation in neuron surrounding cells including but not restricted to glial cells by inhibiting tyrosine kinases or Sirtuin 2.

V. The method of aspects I and III, wherein said neurodegeneration which have chronic or acute levels of inflammation and inflammatory markers surrounding neurons compared to normal state is selected from the group consisting of Parkinson's disease, Alzheimer's disease, Huntington's disease and amyotrophic lateral sclerosis.

VI. Prophylactic or therapeutic use of a compound within family, of either Tyrosine Kinase Inhibitors or Sirtuin 2 Inhibitors, or their stereoisomers, pharmaceutically acceptable salts, polymorphs, solvates and hydrates thereof, for preventing and/or treating neurodegeneration induced by neuroinflammation, in a subject in need thereof comprising: administering to a neurodegeneration high risk subject a prophylactically effective amount.

A more complete understanding can be obtained by reference to the following specific examples, which are provided for purposes of illustration only and are not intended to limit the scope of the disclosure.

EXAMPLES

The present disclosure presents the various aspects of the invention by way of the following examples, wherein Example 1 relates to effect of Tyrosine Kinase Inhibitor and Sirtuin-2 Inhibitor on mice Glial cells (BV2) cells treated with LPS (lipopolysaccharide). Effect of NAC, Tyrosine Kinase Inhibitor and Situin-2 Inhibitor on Neuron-Microglia co-culture (of N27 and BV2 cells) are provided in Example 2, wherein the effect of said compounds is determined on neuronal cell death and nitrite release. Effect of Tyrosine Kinase Inhibitor and Situin-2 Inhibitor on Neuron-Microglia co-culture (of N27 and BV2 cells) are provided in Examples 3-5, wherein the effect of the said inhibitors/compounds is determined on neuronal cell death, nitrite release, IL-6 secretion and MCP-1 secretion induced by inflammatory factors secreted by glial cells. Example 6 provides for the effect of Tyrosine Kinase Inhibitor and Sirtuin-2 Inhibitor in LPS induced nF-κB activity in HEK-Blue™ TLR4/TLR2 cell line. Example 7 depicts that Tyrosine Kinase Inhibitor and Sirtuin-2 Inhibitor have no neuroprotective effect in an oxidative stress model (i.e. Hydrogen Peroxide and MPP+ induced neurotoxicity in N27 cells). For in vitro studies, the experiments are carried out by dissolving the tyrosine kinase inhibitors and Sirtuin 2 inhibitor in dimethyl sulfoxide (DMSO); the LPS is dissolved in sterile water. The protocol for evaluating the effect of Tyrosine Kinase Inhibitor and Sirtuin-2 Inhibitor on the brain of LPS induced mice is provided in example 8. For in vivo studies, the LPS is dissolved in PBS; the vehicle for ND1 and ND2 are about 5% DMSO in PBS.

Materials and Methods

Reagents:

All chemicals, Lipopolysaccharide O111:B4 were purchased from Sigma-Aldrich (St Louis, Mo.). Pam3CSK4, PolyI:C and HEK-Blue Detection media were obtained from InvivoGen (San Diego, Calif.).

Cell Culture:

The immortalized rat mesencephalic dopaminergic cells (N27 cells) were grown in RPMI 1640 medium containing 10% Fetal Bovine Serum (FBS), 2 mM L-glutamine, 50 U Penicillin and 50 μg/ml Streptomycin [22]. Mice microglial cells (BV2 cells) were grown in RPMI 1640 medium containing 10% Heat Inactivated Fetal Bovine Serum (HI-FBS). Cells were maintained in a humidified atmosphere of 5% $CO_2$ at 37° C. until they were 60-70% confluent.

Treatment Paradigm:

Cells at 60-70% confluency were harvested and seeded in 96 well plates at a seeding density of $8 \times 10^3$ cells/well.

Neuron-Microglia Co-Culture:

N27 and BV2 cells (from Iowa State University of Science and Technology, USA) were co-cultured in Corning HTS Transwell Plates, N27 in the lower well of the 24 well plates and BV2 in the 0.4 μm porous permeable support inserted on top of the 24 well. BV2 cells were treated with LPS 1 μg/ml in the presence and absence of specified inhibitors of tyrosine kinase and Sirtuin-2 for 12 hours to 72 hours, preferably 30 hours at 37° C., 5% $CO_2$. The survival of the N27 cells was then measured using MTS Assay. Media was collected from all conditions and tested for concentration of Nitric oxide using the Griess Assay as well as for cytokine profile using Luminex multiplexing assay. Griess Assay and Luminex multiplexing Assay, is performed according to the protocol given by the manufacturer.

Media Transfer Assay:

BV2 Cells were cultured in 96-well plates at seeding of $1 \times 10^4$ cells/well and treated with LPS 1 g/ml in the presence and absence of compounds for 48 hours. The media was then transferred to N27 cells cultured in 96-well plates at seeding of $8 \times 10^3$ cells/well for 24 hours. N27 cell survival was then measured using MTS assay which was performed according to the protocol given by the manufacturer.

HEK-Blue™ TLR2/3/4 Assay:

Hek-Blue TLR-2, TLR-3 and TLR-4 Cells were obtained from InvivoGen (San Diego, Calif.). Culture treatment and assay was performed as per the manufacturers recommended protocol. Cells were treated and incubated for 12 hours, followed by collection of OD values at 620 nm.

Oxidative Stress Model (Hydrogen Peroxide):

Cells were co-treated with 75 μM $H_2O_2$ in the presence and absence of compounds for 8 hours. Treatments were made in complete RPMI medium containing 2% FBS. Cell survival was measured using MTS assay which was performed according to the protocol given by the manufacturer.

Neurotoxin Model (MPP+):

Cells were co-treated with 300 μM MPP+ in the presence and absence of compounds for 24 hours. Treatments were made in complete RPMI medium containing 2% FBS. Cell survival was measured using MTS assay which was performed according to the protocol given by the manufacturer.

Statistical Analysis:

All the data was analyzed using Prism 6.0 Software (GraphPad, San Diego, Calif.) using one-sample t-test.

Example 1: Anti-Neuroinflammatory Effect of Tyrosine Kinase and Situin-2 Inhibitors BV2 (Mice Glial Cells) cells were treated with LPS at a concentration of 1 µg/ml in the presence or absence of test compounds PD180970 or AGK-2 at a concentrating ranging from 0.1 nM-10 Mm and incubated for 48 hours at 37° C. at 5% $CO_2$. Griess assay was used to measure nitrite released in order to investigate the anti-inflammatory potential of the compounds. Untreated BV2 cells was used as blank, 0.1% DMSO in media was used as vehicle. LPS (1 µg/ml) was used as control for nitrite release. FIG. 1 shows the effect of a 48 hr co-treatment of the compounds with LPS on BV2 Cells. Data represents the group mean±SEM; n=4 per condition and experiments were repeated three times. # (P<0.01) indicates significant difference compared to blank control cells. * (P<0.01); * (P<0.001); * (P<0.0001) indicates significant difference compared to LPS treated cells.

PD180970 and AGK-2 were observed to have anti-inflammatory effect on LPS induced inflammation in BV2 cells. PD180970 and AGK-2 caused significant reduction in levels of nitrite, a measure of inflammation, as compared to LPS alone in glial cells, and hence show significant anti-neuroinflammatory effect.

Example 2

Example 2.1: Neuroprotective Effect of NAC, Tyrosine Kinase Inhibitor and Situin-2 Inhibitor on Neuron-Microglia Co-Culture N27 (Rat Dopaminergic cells) and BV2 (Mice Glial Cells) cells were co-cultured in Corning HTS Transwell Plates in RPMI Complete media supplemented with 10% HI-FBS, N27 in the lower well of the 24 well plates and BV2 in the 0.4 µm porous permeable support inserted on top of the 24 well for 24 hours at 37° C., 5% $CO_2$. BV2 cells were treated with 1 µg/ml LPS in the presence and absence of 10 µM of CCND-01, CCND-02, CCND-03 and CCND-04, and 10 mM of NAC for 30 hours at 37° C., 5% $CO_2$. The survival of N27 cells was then measured by performing MTS Assay and taking readings at 490 nm after 30 mins of incubation. Media was collected from all conditions and tested for concentration of Nitric oxide using the Griess Assay as well as for cytokine profile using Luminex multiplexing assay.

CCND-03 and CCND-04 are used as negative controls. CCND-03 is 6-bromoindirubin-3'-oxime (BIO), a potent, reversible and ATP-competitive GSK-3α/β inhibitor and the first pharmacological agent shown to maintain self-renewal in human and mouse embryonic stem cells. CCND-04 is XCT790, a potent and specific inverse agonist of ERRα. CCND-04 is selective; showing no significant antagonist activity on related nuclear receptors, such as ERRγ or ERα at concentrations below 10 µM.

Figure 2A:
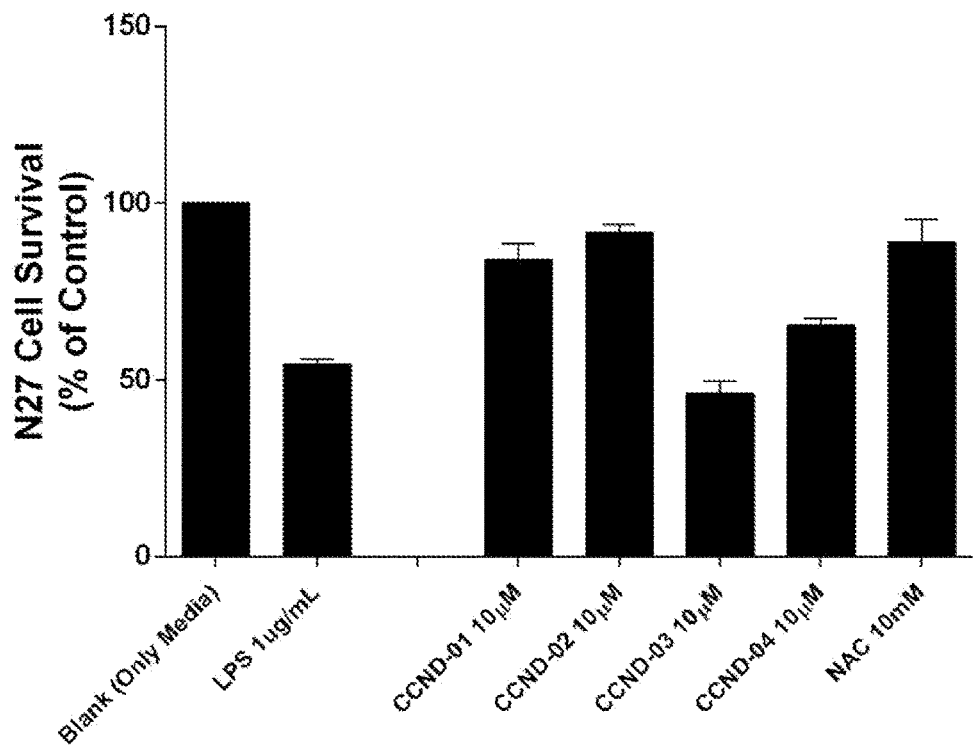
FIG. 2(A) depicts neuroprotective effect of compounds CCND-01 (Tyrosine Kinase inhibitor), CCND-02 (Sirt-2 inhibitor) and NAC in Neuron-Microglia co-culture assay and shows that in accordance with the embodiments of the present invention CCND-01, CCND-02 and NAC inhibit neuronal cell death induced by inflammatory factors secreted by glial cells.

FIG. 2(A) shows the neuroprotective effect of CCND-1, CCND-2 and NAC in toxicity induced by LPS activated BV2 cells. All the data was analyzed using Prism 6.0 Software (GraphPad, San Diego, Calif.) using one-sample t-test. LPS treated BV2 cells caused ~50% cell death in N27 cells in 30 hours. CCND-1, CCND-2 and NAC reduce inflammation and inhibit neuronal cell death induced by inflammatory factors secreted by glial cells. Hence, both CCND-1 and CCND-2 had significant neuroprotective effect in N27 cells.

Example 2.2: Reduction in LPS Induced Nitrite Release

Figure 2B:
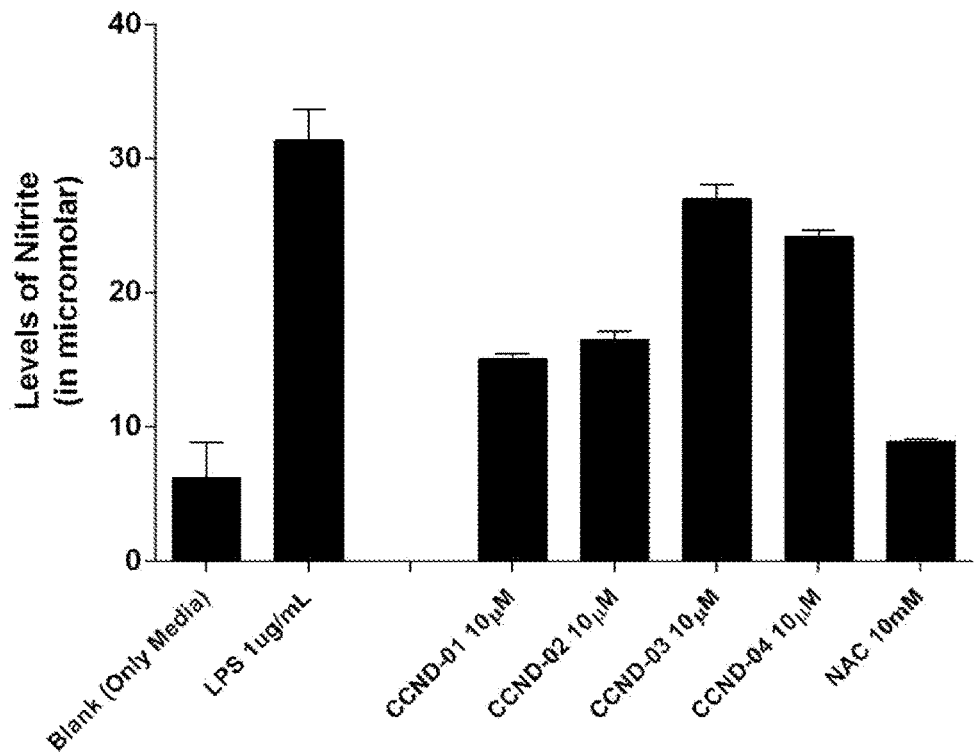
FIG. 2(B) depicts neuroprotective effect of compounds CCND-01 (Tyrosine Kinase inhibitor), CCND-02 (Sirt-2 inhibitor) and NAC in Neuron-Microglia co-culture assay and shows that in accordance with the embodiments of the present invention CCND-01, CCND-02 and NAC inhibit nitrite release.

N27 and BV2 co-culture in Corning HTS Transwell Plates, N27 in the lower well of the 24 well plates and BV2 in the 0.4 µm porous permeable support inserted on top of the 24 well were treated with 1 µM of CCND-01, CCND-02, CCND-03 and CCND-04, and 10 mM of NAC, in the presence of LPS 1 µg/ml for 30 hours and assayed for Nitrite release. LPS (1 µg/ml) treated BV2 cells was used as control for nitrite release. Griess assay was performed to determine the concentration of Nitrite released by BV2. FIG. 2(B) shows the anti-nitrite effect of CCND-01, CCND-02 and NAC in LPS activated BV2 cells. LPS (1 µg/ml) was used as an inflammation inducer causing nearly 50% death in N27. CCND-01, CCND-02 and NAC caused significant reduction in level of nitrite released by LPS induced BV2 cells. Thus, co-treatment of CCND-01, CCND-02 and NAC with LPS caused significant increase in neuronal survival as compared to LPS alone.

Figure 3:
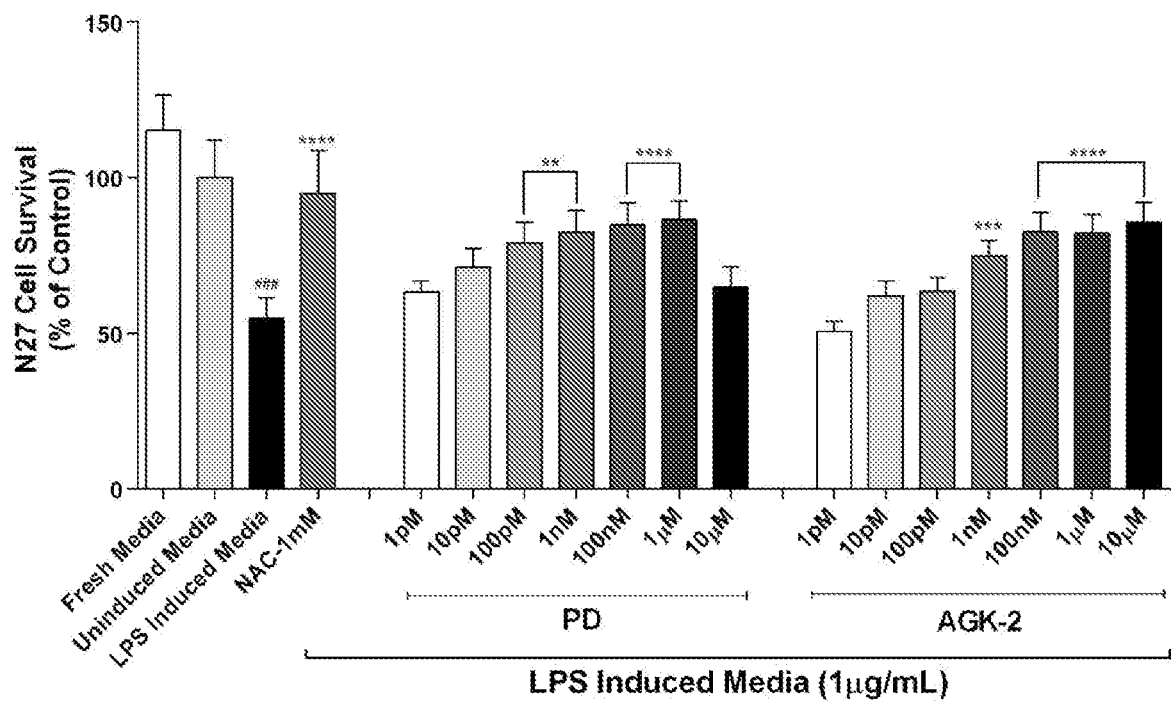
FIG. 3 depicts the neuroprotective effect of NAC, CCND-01 and CCND-02 in toxicity induced by conditioned media from LPS activated BV2 cells.

Example 3: Effect of NAC, Tyrosine Kinase and Situin-2 Inhibitors on Neuron-Microglia Co-Culture N27 and BV2 cells were co-cultured in Corning HTS Transwell Plates, N27 in the lower well of the 24 well plates and BV2 in the 0.4 µm porous permeable support inserted on top of the 24 well. BV2 cells were treated with 1 µg/ml LPS in the presence and absence of 10 µM of PD180970 and AGK-2 or in presence of 1 mM NAC, and incubated for 30 hours. The survival of N27 cells was measured by performing MTS Assay and taking readings at 490 nm after 30 mins of incubation. The results are depicted in FIG. 3, wherein neuroprotective effect of PD180970 and AGK-2 in toxicity induced by LPS activated BV2 cells is illustrated. Fresh media refers to RPMI media which hasn't been put on cells. Uninduced media refers to RPMI which has been added to BV2 cells without any LPS/treatment and incubated for 48 hours. LPS (1 µg/ml) treated BV2 cells was used as control. LPS treated BV2 cells caused ~50% cell death in N27 cells in 30 hours. NAC, PD180970 and AGK-2 had significant neuroprotective effect in N27 cells.

Example 4: Neuroprotective Effect of NAC, Tyrosine Kinase and Situin-2 Inhibitors on Neuron-Microglia Co-Culture

Example 4.1: Effect on Cell Viability

Figure 4:
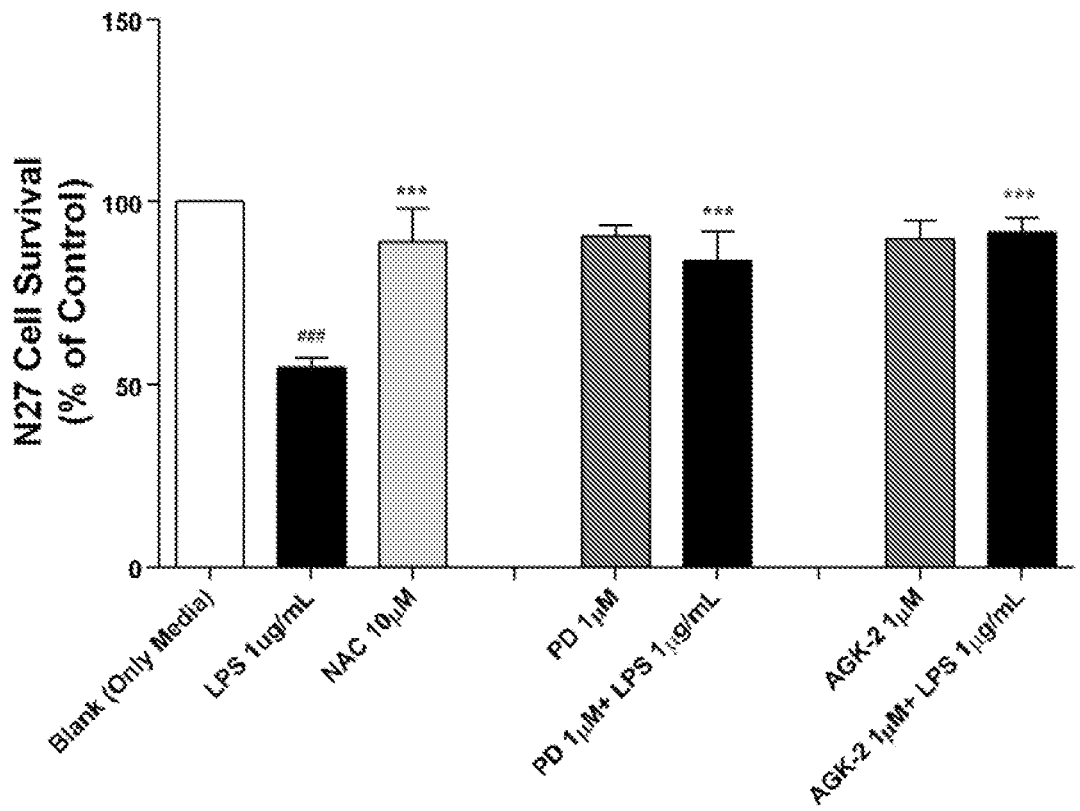
FIG. 4 depicts neuroprotective effect of compounds on LPS induced neuronal death in N27-BV2 Co-culture.

N27 and BV2 cells were co-cultured in Corning HTS Transwell Plates, N27 in the lower well of the 24 well plates and BV2 in the 0.4 µm porous permeable support inserted on top of the 24 well were treated with 1 µM of compounds PD180970 and AGK-2 and 10 µM of compound NAC, in the presence and absence of LPS 1 µg/ml, and assayed for N27 cell survival at 30 hours. Treating the cells with the test compounds alone (without LPS) shows if the compounds are toxic or inflammatory by themselves or not. LPS (1 µg/ml) treated BV2 cells was used as control for nitrite release. MTS assay was performed to determine the percentage N27 survival. FIG. 4 shows the neuroprotective effect of PD180970 and AGK-2 in toxicity induced by LPS activated BV2 cells. Data represents the group mean±SEM; n=4 per condition and experiments were repeated three times. #### (p<0.001) indicates significant difference compared to blank control cells. *** (p<0.001) indicates significant difference compared to LPS treated cells.

LPS treated BV2 cells caused ~50% cell death in N27 cells in 30 hours. Treatment of cells with PD180970 and AGK2 alone had no effect, indicating that PD180970 and AGK2 do not have any effect on the cells, their survival, nitrite release or morphology. Co-treatment of PD180970/

AGK-2 with LPS caused significant decrease in nitrite level as compared to LPS alone. NAC, PD180970 and AGK-2 had significant protective effect in N27 cells.

Figure 5:
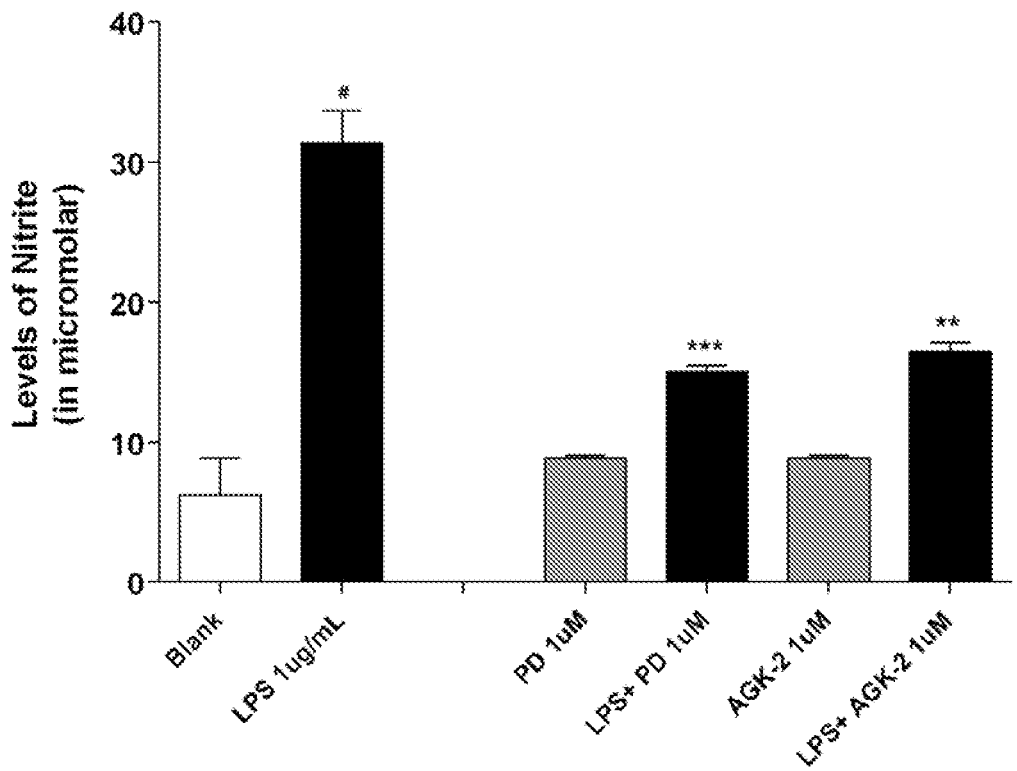
FIG. 5 depicts anti-inflammatory response of compounds on LPS induced Nitrite release in N27-BV2 Co-culture.

Example 4.2: Reduction in LPS Induced Nitrite Release by BV2 Cells in Neuron-Microglia Co-Culture N27 and BV2 co-culture in Corning HTS Transwell Plates, N27 in the lower well of the 24 well plates and BV2 in the 0.4 µm porous permeable support inserted on top of the 24 well were treated with 1 µM of compounds PD180970 and AGK-2, in the presence and absence of LPS 1 µg/ml for 30 hours and assayed for Nitrite release. LPS (1 µg/ml) treated BV2 cells was used as control for nitrite release. Griess assay was performed to determine the concentration of Nitrite released by BV2. FIG. 5 shows the anti-nitrite effect of PD180970 and AGK-2 in LPS activated BV2 cells. Data represents the group mean±SEM; n=4 per condition and experiments were repeated three times. ### ($p<0.001$) indicates significant difference compared to blank control cells. *** ($p<0.001$) indicates significant difference compared to LPS treated cells.

PD180970 or AGK2 alone had no effect themselves on the cells, survival, nitrite release or morphology. LPS (1 µg/ml) was used as an inflammation inducer causing nearly 50% death in N27. Both PD180970 and AGK-2 at 1 µM caused significant reduction in level of nitrite released by LPS induced BV2 cells. Co-treatment of PD180970/AGK-2 with LPS caused significant increase in neuronal survival as compared to LPS alone.

Example 4.3: Reduction in LPS Induced Release of IL-6 and MCP-1 by BV2 Cells in Neuron-Microglia Co-Culture N27 and BV2 co-culture in Corning HTS Transwell Plates, N27 in the lower well of the 24 well plates and BV2 in the 0.4 µm porous permeable support inserted on top of the 24 well were treated with 1 µM of compounds PD180970 and AGK-2, in the presence and absence of LPS 1 µg/ml for 30 hours. LPS (1 µg/ml) treated BV2 cells was used as control. Luminex multiplexing assay was performed to determine the concentration of IL-6 and MCP-1 released. LPS (1 µg/ml) was used as control for IL-6 release or MCP-1 release.

Figure 6:
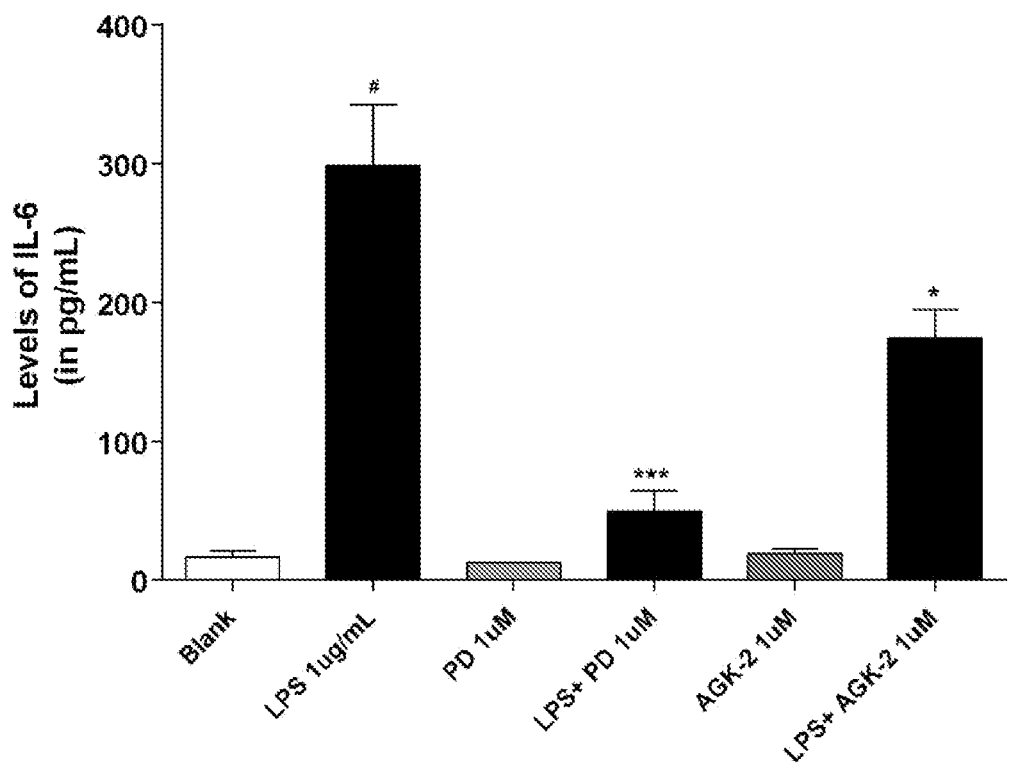
FIG. 6 depicts anti-inflammatory response of compounds on LPS induced IL-6 secretion by BV2 in N27-BV2 Co-culture.
Figure 7:
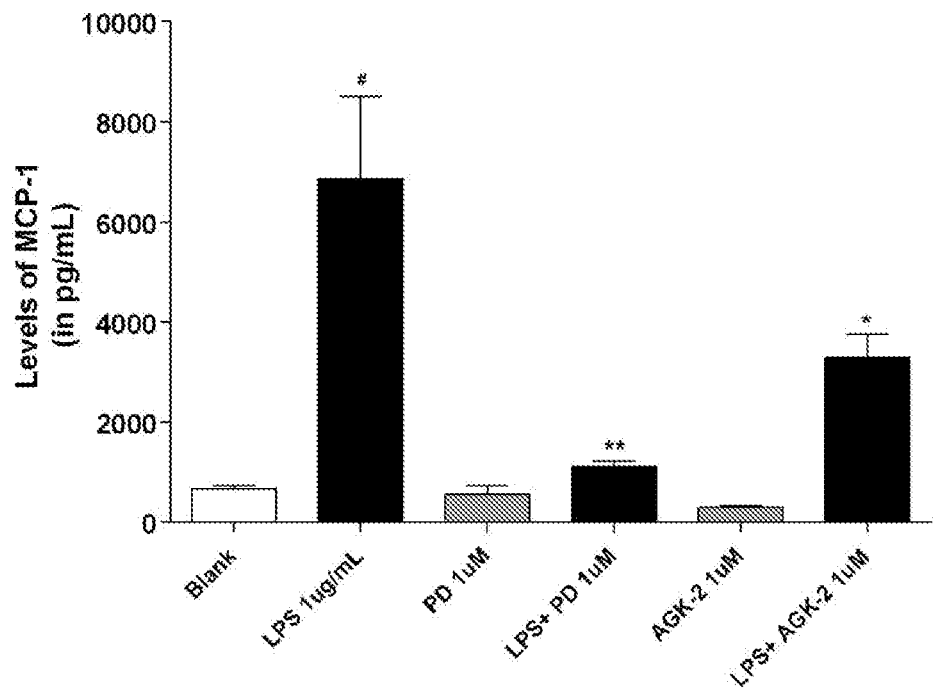
FIG. 7 depicts anti-inflammatory response of compounds on LPS induced MCP-1 secretion by BV2 in N27-BV2 Co-culture.

PD180970 or AGK2 alone had no effect themselves on the cells, survival, nitrite release or morphology. LPS treated BV2 cells caused considerable increase in the levels of IL-6 and MCP-1 secreted by BV2 cells at 30 hours. Both PD180970 and AGK-2 at 1 µM caused significant reduction in level of IL-6 released by LPS induced BV2 cells. Reduction in IL-6 ameliorates neuronal survival. FIG. 6 shows the reduction in the levels of IL-6 due to PD180970 and AGK-2 in LPS activated BV2 cells. FIG. 7 shows the reduction in the levels of MCP-1 due to PD180970 and AGK-2 in LPS activated BV2 cells. PD180970 and AGK-2 caused significant reduction in levels of IL-6 and MCP-1 as compared to LPS alone. Data represents the group mean±SEM; n=4 per condition and experiments were repeated three times. # ($p<0.01$) indicates significant difference compared to blank control cells. * ($p<0.01$); *** ($p<0.001$); indicates significant difference compared to LPS treated cells.

Figure 8:
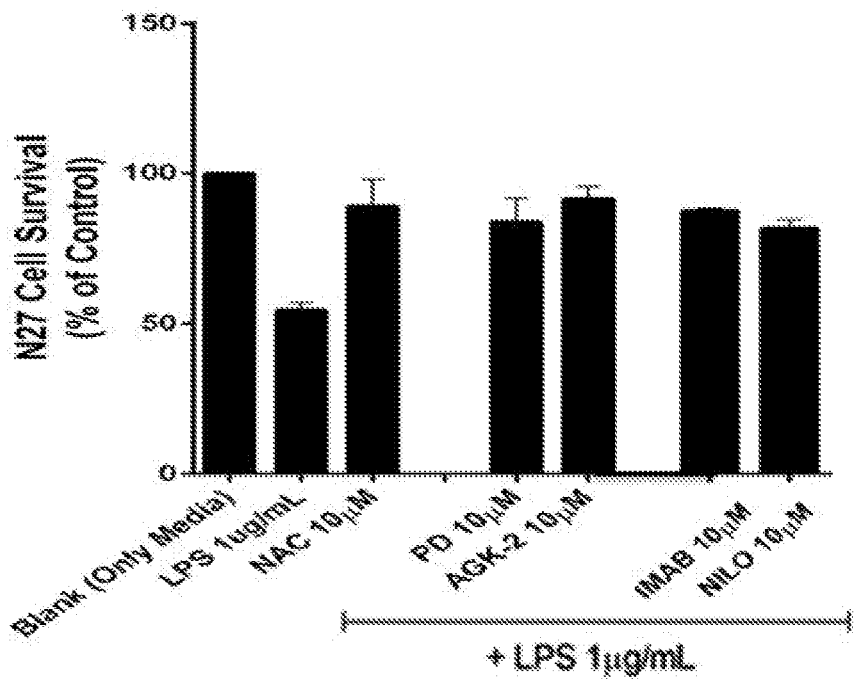
FIG. 8 depicts the neuroprotective effect of NAC, the Bcr-Abl TK inhibitors (CCND-01, Imatinib and Nilotinib) and Sirtuin-2 inhibitor (AGK-2) in toxicity induced by LPS activated BV2 cells.

Example 5: Effect of NAC, Various Tyrosine Kinase Inhibitors and Situin-2 Inhibitor on Neuron-Microglia Co-Culture N27 and BV2 co-cultures in Corning HTS Transwell Plates, N27 in the lower well of the 24 well plates and BV2 in the 0.4 µm porous permeable support inserted on top of the 24 well were treated with LPS 1 µg/ml in the presence of 10 µM Tyrosine Kinase Inhibitors PD180970, Imatinib (IMAB) or Nilotinib (NILO), or 10 µM of Sirtuin-2 inhibitor AGK-2, 10 µM of NAC was treated BV2 cells, and incubated for 30 hours. LPS (1 µg/ml) treated BV2 cells was used as control for nitrite release. MTS assay was performed to determine the percentage N27 survival. FIG. 8 shows the neuroprotective effect of the Bcr-Abl TK inhibitors and Sirtuin-2 inhibitor in toxicity induced by LPS activated BV2 cells. LPS treated BV2 cells caused ~50% cell death in N27 cells in 30 hours. NAC indicated neuroprotective role. Bcr-Abl Tyrosine Kinases PD180970, Imatinib and Nilotinib and Sirtuin-2 inhibitor AGK-2 at 10 µM had significant protective effect in N27 cells. The survival of cells (with LPS) treated with the Tyrosine Kinase Inhibitors and Sirtuin-2 inhibitors (having cell survival of over 75%) significantly increased compared to the LPS cells not treated with the compounds (having cell survival of only about 50%), implicating the neuroprotective role of the former.

Example 6: Reduction in LPS Induced nF-κB Activity in HEK-Blue™ TLR4 Cell Line

Figure 9:
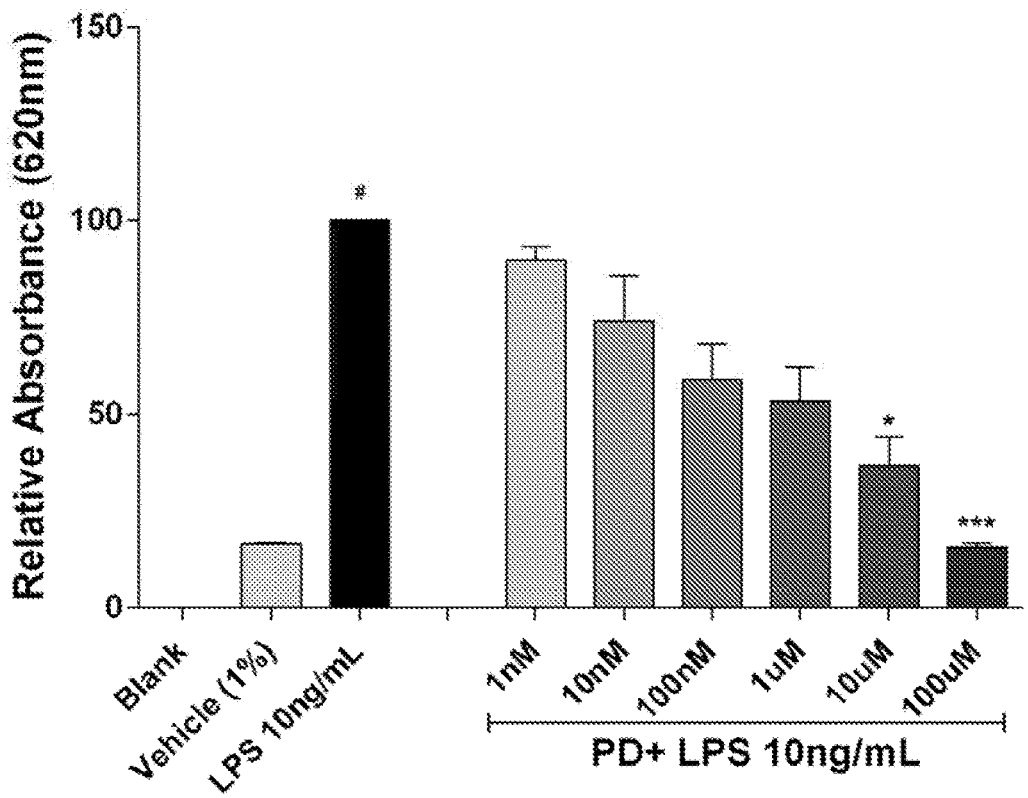
FIG. 9 depicts anti-inflammatory response of CCND-01 on nF-κB induced SEAP activity in HEK-Blue™ TLR4 Cell Line.
Figure 10:
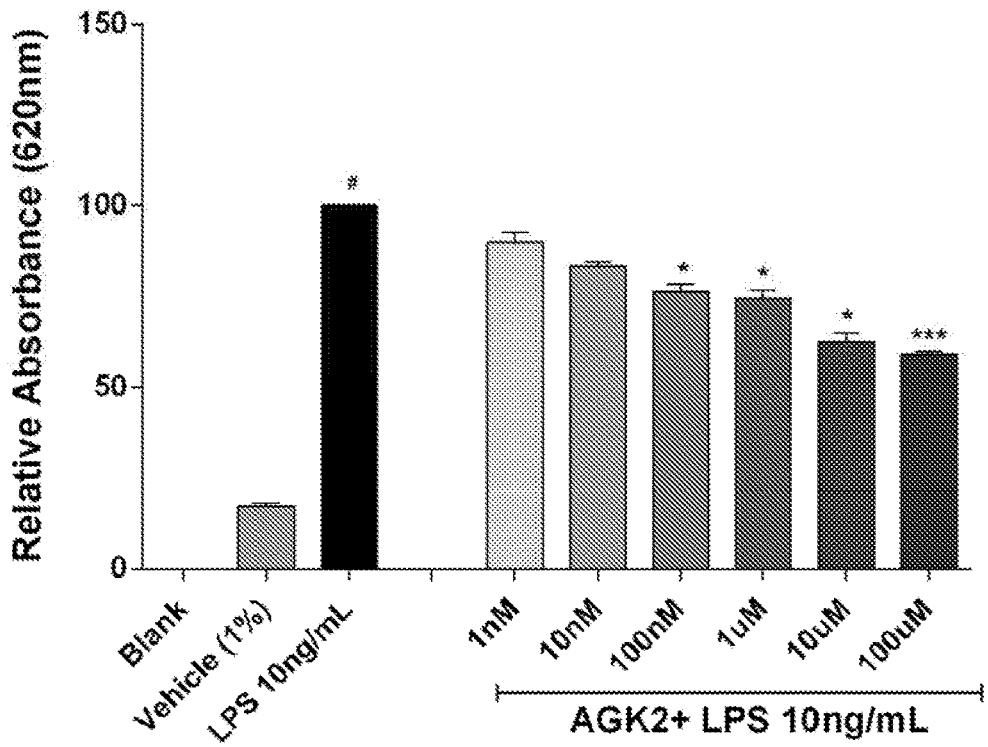
FIG. 10 depicts anti-inflammatory response of AGK2 on nF-κB induced SEAP activity in HEK-Blue™ TLR4 Cell Line.

HEK-Blue™ TLR4 cells were treated with LPS and HEK-Blue™ TLR2 were treated with Pam3CSK4 at a concentration of 10 ng/ml for 12 hours in the presence or absence of compounds (PD180970 or AGK-2) at a range of 1 nM-100 µM, and assayed for SEAP activity. LPS (long/ml) was used as control for SEAP activity. nF-κB induced SEAP activity was quantified using HEK-Blue™ Detection at 620 nm. FIG. 9 shows the effect of a 12 hr co-treatment of PD180970 with LPS 10 ng/ml on HEK-Blue™ TLR4 Cells. FIG. 10 shows the effect of a 12 hr co-treatment of AGK-2 with LPS 10 ng/ml on HEK-Blue™ TLR4 Cells. Data represents the group mean±SEM; n=4 per condition and experiments were repeated three times. # ($P<0.01$) indicates significant difference compared to blank control cells. * ($P<0.001$); *** ($P<0.0001$) indicates significant difference compared to LPS treated cells.

PD180970 and AGK-2 co-treated with LPS 10 ng/ml caused significant reduction in levels of nF-κB induced SEAP as compared to LPS alone. PD180970 and AGK-2 were observed to have significant inhibitory effect on nF-κB induced SEAP activity in HEK-Blue™ TLR4 cells but not in HEK-Blue™ TLR2 cells, suggesting that these compounds work through the TLR4 pathway and not through the TLR2 pathway.

Example 7

Example 7.1: Tyrosine Kinase Inhibitors and Sirtuin-2 Inhibitors do not Show Neuroprotective Effect on $H_2O_2$ Induced Dopaminergic Cell Death (Oxidative Stress Model)

Figure 11:
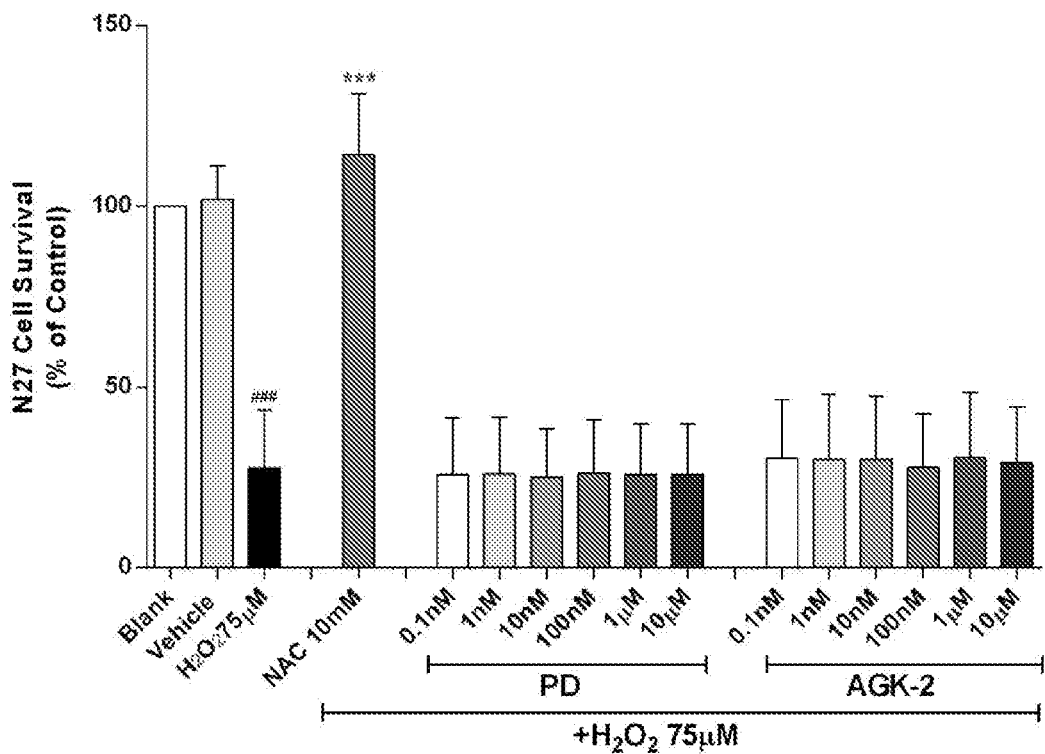
FIG. 11 depicts effect of compounds against hydrogen peroxide induced neurotoxicity in N27 cells.

N27 cells were treated with 75 µM hydrogen peroxide in the presence and absence of compounds PD180970 or AGK2 in a concentration range of 0.1 nM-10 µM for 8 hours in 96 well plates. MTS assay was used to check the cell viability in order to investigate the neuroprotective potential of the compounds. Cells with untreated media was used as blank, and cells with media containing 0.1% DMSO (vehicle or solvent for the compounds) was used as vehicle. Hydrogen peroxide (75 µM) treated N27 cells was used as control for. FIG. 11 shows the effect of screening of compounds against hydrogen peroxide induced neurotoxicity for 8 hours on N27 cells. Data represents the group mean±SEM; n=4 per condition and experiments were repeated three times. ### (P<0.001) indicates significant difference compared to blank control cells; *** (P<0.001) indicates significant difference compared to $H_2O_2$ treated cells. Neither of the compounds were able to rescue the neurons from degeneration as they were observed to have no significant neuroprotective effect on $H_2O_2$ induced toxicity in N27 cells.

Example 7.2: Tyrosine Kinase Inhibitors and Sirtuin-2 Inhibitors do not Show Neuroprotective Effect on MPP+ Induced Dopaminergic Cell Death (Oxidative Stress Model)

Figure 12:
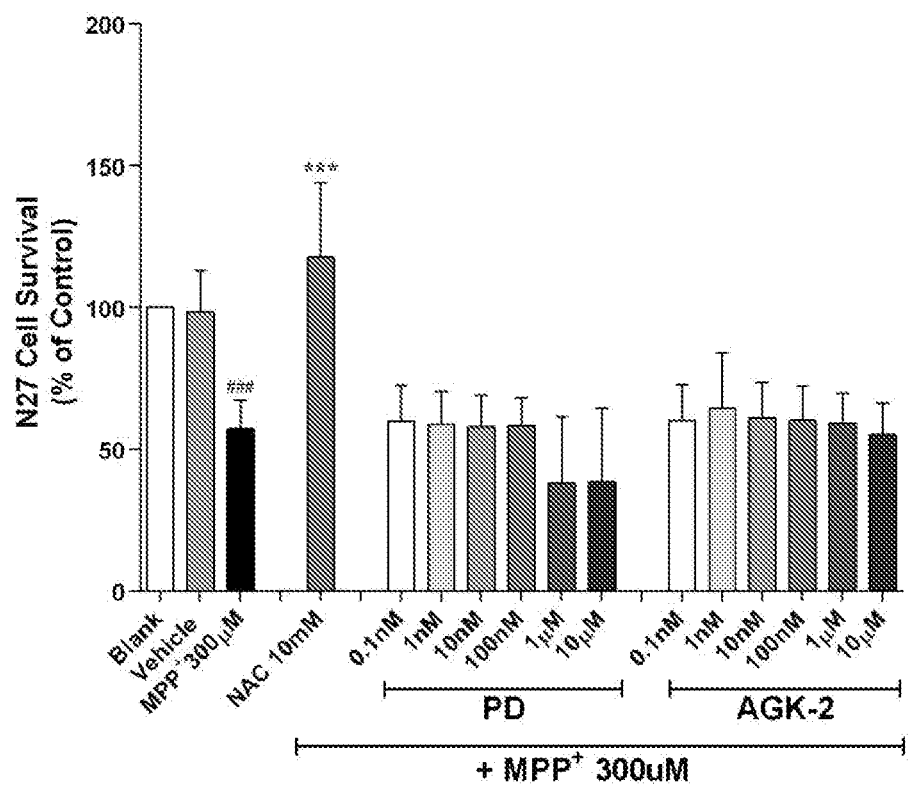
FIG. 12 depicts effect of compounds against MPP$^+$ induced neurotoxicity in N27 Cells.

N27 cells were treated with 300 μM of MPP+ in the presence and absence of compounds (PD180970 or AGK-2) in a concentration range of 0.1 nM-10 μM and incubated for 24 hours. MPP+ (300 μM) treated N27 cells was used as control. MTS assay was used to check the cell viability in order to investigate the neuroprotective potential of the compounds. None of the compounds could rescue MPP+ treated dopaminergic N27 cells. FIG. 12 shows the effect of screening of 4 compounds against MPP+ induced neurotoxicity for 24 hours on N27 cells. Data represents the group mean±SEM; n=4 per condition and experiments were repeated three times. ### (P<0.001) indicates significant difference compared to blank control cells; *** (P<0.001) indicates significant difference compared to MPP+ treated cells. None of the compounds showed rescue of neurons and were hence observed to have no significant neuroprotective effect on MPP+ induced toxicity in N27 cells.

Thus, from the above results it is observed that Tyrosine Kinase Inhibitors and Sirtuin-2 inhibitors are unable to inhibit neuron degeneration caused due to oxidative stress or toxicity. However, these compounds have anti-neurodegenerative effect on neurons, as illustrated in examples 1-5, by stopping neuronal death induced by inflammation in neuron surrounding cells including but not restricted to glial cells, by inhibiting tyrosine kinases or Sirtuin-2.

Example 8: Anti-Neuroinflammatory and Neuroprotective Effects of Test Compounds in Mice Effect of the test compounds on brain (SNPc) in LPS induced mice [C57BL/6, Male, about 10-12 weeks, about 28-30 g] is evaluated. All animals are acclimatized for about five days before experiment and randomized according to body weight in to about 8 groups. The animals are treated with test compounds and LPS as specified in Experimental design in table 1. Behavioral tests, Force swim test (FST) and Rotarod test, is performed for all the groups once in two days throughout the experiment. About ten animals from each group are sacrificed on about days 6 and 19.

TABLE 1

Experimental Design

| Groups | Treatment# Group | Dose/Route/ Regimen | Day 6 Sac [no mice] | | Day 19 sac [no mice] mRNA from brain tissue | |
|---|---|---|---|---|---|---|
| | | | Snpc Microtomy sections - IHC | m-RNA for RT - PCR | Snpc Microtomy sections - IHC | m-RNA for RT - PCR |
| I | Normal Control | (Vehicle/Saline) | 5 + 5 | 5 + 5 | 5 + 5 | 5 + 5 |
| II | LPS alone | 40 μg/kg, IP, qd [days 2, 3, 4, 5] | 5 + 5 | 5 + 5 | 5 + 5 | 5 + 5 |
| III | ND1 Alone | 5 mg/kg, IP, qd, [days 0, 1, 2, 3, 4, 5] | 5 + 5 | 5 + 5 | 5 + 5 | 5 + 5 |
| IV | ND2 Alone | 5 mg/kg, IP, qd, [days 0, 1, 2, 3, 4, 5] | 5 + 5 | 5 + 5 | 5 + 5 | 5 + 5 |
| V | Pre-treatment ND1 + LPS | ND1 - 5 mg/kg, IP, days0, 1, 2, 3, 4, 5 + LPS, 40 μg/kg, IP, days 2, 3, 4, 5 | 5 + 5 | 5 + 5 | 5 + 5 | 5 + 5 |
| VI | Co-treatment ND1 + LPS | ND1 - 5 mg/kg, IP, days 2, 3, 4, 5 + LPS 40 μg/kg, IP, days 2, 3, 4, 5 | 5 + 5 | 5 + 5 | 5 + 5 | 5 + 5 |
| VII | Pre-treatment ND2 + LPS | ND2 - 5 mg/kg, IP, days0, 1, 2, 3, 4, 5 + LPS 40 μg/kg, IP, days 2,3,4,5 | 5 + 5 | 5 + 5 | 5 + 5 | 5 + 5 |
| VIII | Co-treatment ND2 + LPS | ND2 - 5 mg/kg, IP, days 2, 3, 4, 5 + LPS 40 ug/kg, IP, days 2, 3, 4, 5 | 5 + 5 | 5 + 5 | 5 + 5 | 5 + 5 |

Test compounds: LPS (sigma: O11B4) ND1 (PD180970) & ND2 (AGK-2)
Feed status: Feed and water will be provided ad libitum
Tissues for collection: Brain Formulation Preparation:
The vehicle for LPS is PBS. The vehicle for ND1 and ND2 is about 5% DMSO in PBS.
The final concentration needed for a about 5 mg/kg dose is about 1 mg/ml in about 5% DMSO+about 95% PBS. The dose volume given is about 5 ml/kg.

Forced Swim Test (FST):
The forced swim test is carried out on mice individually. Mice are made to swim in an open cylindrical container (diameter about 10 cm, height about 25 cm), containing about 15 cm of water at about 25±1° C.; the total duration of immobility during the about 6-min test is scored. Each mouse is judged to be immobile when it ceases struggling and remains floating motionless in the water, making only those movements necessary to keep its head above water. The duration of immobility is recorded.

Rotarod Test:

Training Procedure:

All the animals are trained in a group of about 5 for 5 consecutive days, before the day of injection.

Five animals are placed on non-rotating rotarod simultaneously and allowed to balance themselves on the rod. The following training plan (table 2) is followed:
1. The rotarod is started at an appropriate speed (according to the training plan) and the speed is increased up to a certain higher rpm based on training plan specified above by accelerating at the rate of about 1 rpm per 5 seconds (for training day 4 and 5 a fixed rpm of about 20 is used). Till the speed reaches to the higher rpm, all the animals are put back on the rotating rotarod, if they fall down
2. Once the speed of rotarod reaches to the higher rpm, animals are given a span of about 5 seconds to maintain themselves. All the animals, which fall down during this span of about 5 seconds are placed back on the rotating rota rod.
3. After the span of 5 seconds, the higher rpm is maintained for about 1 minute and the animals which will fall down within this time, are removed and put back to their respective cages
4. The above procedure is repeated for all the animals of each individual group by giving an inter-trial interval of about 5 minutes.

TABLE 2

Training plan

| Day | Speed of the rotarod (rpm) | Acceleration (increase in rpm/5 sec) |
|---|---|---|
| 1 | 5-10 | 1 rpm/5 sec |
| 2 | 7-15 | 1 rpm/5 sec |
| 3 | 10-20 | 1 rpm/5 sec |
| 4 | 20 | 0 |
| 5 | 20 | 0 |

Experimental Procedure:
1. At one time, about five animals are placed on non-rotating rotarod until they are able to balance themselves on the rod.
2. The rotarod is directly started at about 20 rpm. Animals are given a span of about 5 seconds to maintain themselves at about 20 rpm. All the animals, which fall down during this span of about 5 seconds are placed back on the rotating rota rod.
3. After the span of about 5 seconds, the 20 rpm speed is maintained for about 1 minute and the animals which will fall down within this time, are removed and put back to their respective cages.
4. The above procedure from step 2 to step 3 is repeated three times for each individual group of animals by giving an inter-trial interval of about 5 minutes.
5. The mean latency to fall is calculated by taking the average of all three trials for each individual animal.

Brain Collection to Study mRNA Level:
1. Before excising the tissue sample, the volume (or weight) of the sample to be stabilized in RNA later RNA Stabilization Reagent is estimated.
2. Appropriate volume of RNA later RNA Stabilization Reagent for preserving the tissue is pipetted in to an appropriate collection vessel, or an appropriate size RNAlater Tissue Protect Tube. At least 10 volumes of the reagent (or approximately about 10 µl reagents per 1 mg of tissue) is required.
3. Approximate wt of brain tissue: 500 mg
   For 500 mg; 500×10 ul=5 ml
   For 160 tissues; 80×5 ml=400 ml
4. The tissue sample from the animal is excised and, if necessary, cut it into slices less than about 0.5 cm thick. This step is performed as quickly as possible.
5. The tissue piece(s) is completely submerged, immediately, in the collection vessel containing RNAlater RNA Stabilization Reagent from step 2.

Histopathology:

Post dosing and at the specified time points [days 6 and 19], animals are sacrificed by $CO_2$ asphyxiation.

Fixation Protocol:
1. Mice are perfused transcardially at a flow rate of about 10 ml min' first with 1% cold PBS for about 3 min followed by about 4% paraformaldehyde solution for about 8 min using a peristaltic pump.
2. The brain is removed quickly and immersed overnight in at least ten times the brain's own volume of about 4% paraformaldehyde at about 4° C.
3. The fixed brains is cryoprotected by discarding the fixative solution and replacing it with Cryoprotectant solution. It is important to cryoprotect until the brains sink quickly to the bottom of the container after inversion of the container.

Composition of Cryoprotectant Solution (For about 500 mL):
  Glycerol—About 150 mL
  Ethylene glycol—About 150 mL
  1×PBS—About 200 mL
  Adjust the pH to 7.4.
4. The brain is sectioned using a freezing ultramicrotome or a vibratome.

Freezing ultramicrotome for sectioning: The brain is freezed by immersion in isopentane (2-methylbutane) cooled on powdered dry ice. For best results, insert a thermometer into the isopentane to gauge its temperature. At about −40° C., it takes approximately about 35 s to freeze a mouse's brain. The frozen brains are wrapped in aluminum foil with the sample identification on the outside of the foil and stored at about −80° C. until they are processed. For sectioning, the sections are prepared for immunostaining by solidly bonding whole fixed, frozen brains to the metal object holder with a tissue-freezing medium (e.g., OCT Tissue-Tek) and cut on a cryostat or a freezing-sliding microtome.

Vibratome for sectioning: The brains are immersed in Cryoprotectant solution in glass vials/multiwall plates and stored at about −20° C. until they are processed. For sectioning, the sections are prepared for immunostaining by bonding whole fixed brains to the metal object holder of the vibratome with a tissue-sticking medium (e.g., fevi-quick) and cut on a vibratome for about 30 µm section thickness.

The collected sections (about 30 µm thickness) of the brain tissue, in particular from the Substantia Nigra Pars compacta region-SNPc rich in dopaminergic cells and microglia, are used for immunohistochemistry. The sections should be stored at about −20° C. in the cryoprotectant solution, preferably in 24 well plates (about 20 Sections/well in about 1 mL cryoprotectant solution).

Although the disclosure and exemplification has been provided by way of illustrations and examples for the purpose of clarity and understanding, it is apparent to a person skilled in the art that various changes and modifications can be practiced without departing from the spirit or scope of the disclosure. Accordingly, the foregoing descriptions and examples should not be construed as limiting the scope of the present disclosure.

The description of the embodiments of the present disclosure reveals the general nature of the embodiments that are readily suitable for modification and/or adaptation for various applications by applying the current knowledge. Such specific embodiments of the disclosure, without departing from the generic concept, and, therefore, such adaptations and modifications should and are intended to be comprehended and considered within the meaning and range of equivalents of the disclosed embodiments.

It is also to be understood that the phrases or terms employed herein are for the purpose of description and not intended to be of any limitation. Throughout the present disclosure, the word "comprise", or variations such as "comprises" or "comprising" wherever used, are to be understood to imply the inclusion of a stated element, integer or step, or group of elements, integers or steps, but not the exclusion of any other element, integer or step, or group of elements, integers or steps.

Where a numerical limit or range is stated herein, the endpoints are included. Also, values and sub-ranges within a numerical limit or range are specifically included as if explicitly written out.

With respect to the use of any plural and/or singular terms in the present disclosure, those of skill in the art can translate from the plural to the singular and/or from the singular to the plural as is considered appropriate to the context and/or application. The various singular/plural permutations may be expressly set forth herein for the sake of clarity.

Any discussion of documents, acts, materials, devices, articles and the like that has been included in this specification is solely for the purpose of providing a context for the present disclosure. It is not to be taken as an admission that any or all of these matters form a part of the prior art base or are common general knowledge in the field relevant to the present disclosure, as it existed anywhere before the priority date of this application.

The contents of all references, patents, and published patent applications cited throughout this application are incorporated herein by reference for all purposes.

The invention claimed is:

1. A method of managing neuroinflammation or neuroinflammation mediated neurodegenerative disease or disorder in a subject in need thereof, comprising administering a combination of PD180970 as a tyrosine kinase inhibitor and AGK-2 as a sirtuin-2 inhibitor to the subject in need thereof, wherein the neurodegenerative disease or disorder is Parkinson's disease, Alzheimer's disease, Huntington's disease, multiple sclerosis, or amyotrophic lateral sclerosis.

2. The method as claimed in claim 1, wherein the combination of tyrosine kinase inhibitor and sirtuin-2 inhibitor is administered along with a pharmaceutically acceptable excipient.

3. The method as claimed in claim 2, wherein the pharmaceutically acceptable excipient is selected from the group consisting of granulating agent, binding agent, lubricating agent, disintegrating agent, sweetening agent, glidant, anti-adherent, anti-static agent, surfactant, anti-oxidant, gum, coating agent, coloring agent, flavouring agent, additive, solvent, viscosity enhancer, plasticizer, preservative, suspending agent, emulsifying agent, plant cellulosic material, spheronization agents and combinations thereof.

4. The method as claimed in claim 1, wherein the subject is human.

5. The method as claimed in claim 1, wherein the combination of tyrosine kinase inhibitor and sirtuin-2 inhibitor stops neuronal death induced by inflammation in neuron surrounding cells thereby managing the neuroinflammation or neuroinflammation mediated neurodegenerative disease or disorder in the subject.

6. The method as claimed in claim 5, wherein the neuron surrounding cells are selected from the group consisting of glial cells, astrocytes and immune cells or any combination thereof.

* * * * *